US011235035B2

(12) United States Patent
Romero et al.

(10) Patent No.: US 11,235,035 B2
(45) Date of Patent: *Feb. 1, 2022

(54) FEED ADDITIVE COMPOSITION

(71) Applicant: DUPONT NUTRITION BIOSCIENCES APS, Copenhagen (DK)

(72) Inventors: Luis Romero, Wiltshire (GB); Peter Plumstead, Randburg (ZA); Luke Barnard, Wiltshire (GB)

(73) Assignee: DUPONT NUTRITION BIOSCIENCES APS

( * ) Notice: Subject to any disclaimer, the term of this patent is extended or adjusted under 35 U.S.C. 154(b) by 77 days.

This patent is subject to a terminal disclaimer.

(21) Appl. No.: 16/208,829

(22) Filed: Dec. 4, 2018

(65) Prior Publication Data

US 2019/0167769 A1  Jun. 6, 2019

Related U.S. Application Data

(62) Division of application No. 14/866,533, filed on Sep. 25, 2015, now Pat. No. 10,149,891, which is a division of application No. 13/827,730, filed on Mar. 14, 2013, now Pat. No. 9,179,693.

(30) Foreign Application Priority Data

Aug. 3, 2012 (GB) ................................ 1213801

(51) Int. Cl.
| | |
|---|---|
| *A61K 38/46* | (2006.01) |
| *A61K 35/742* | (2015.01) |
| *A23K 40/25* | (2016.01) |
| *A23K 40/20* | (2016.01) |
| *A23K 10/18* | (2016.01) |
| *A23K 20/174* | (2016.01) |
| *A23K 20/189* | (2016.01) |
| *A23K 20/20* | (2016.01) |
| *A23K 50/75* | (2016.01) |
| *A23K 50/30* | (2016.01) |
| *A61K 35/66* | (2015.01) |

(52) U.S. Cl.
CPC ............ *A61K 38/465* (2013.01); *A23K 10/18* (2016.05); *A23K 20/174* (2016.05); *A23K 20/189* (2016.05); *A23K 20/20* (2016.05); *A23K 40/20* (2016.05); *A23K 40/25* (2016.05); *A23K 50/30* (2016.05); *A23K 50/75* (2016.05); *A61K 35/66* (2013.01); *A61K 35/742* (2013.01); *A61K 38/46* (2013.01); *C12Y 301/03008* (2013.01); *C12Y 301/03026* (2013.01); *C12Y 301/03* (2013.01)

(58) Field of Classification Search
None
See application file for complete search history.

(56) References Cited

U.S. PATENT DOCUMENTS

| | | | |
|---|---|---|---|
| 5,945,333 | A | 8/1999 | Rehberger |
| 6,951,643 | B2 | 10/2005 | Rehberger |
| 7,045,135 | B2 | 5/2006 | Iwasaki |
| 7,317,138 | B2 | 1/2008 | Lanahan et al. |
| 7,354,757 | B2 | 4/2008 | Rehberger |
| 7,384,628 | B2 | 6/2008 | Rehberger |
| 7,432,097 | B2 | 10/2008 | Short et al. |
| 7,470,531 | B2 | 12/2008 | Rehberger |
| 7,632,668 | B2 | 12/2009 | Lanahan et al. |
| 7,754,459 | B1 | 7/2010 | Kock |
| 7,754,469 | B2 | 7/2010 | Baltzley |
| 7,923,232 | B2 | 4/2011 | Lassen et al. |
| 7,932,232 | B2 | 4/2011 | Lassen et al. |
| 8,227,235 | B2 | 7/2012 | Skinner et al. |
| 9,179,693 | B2 | 11/2015 | Romero et al. |
| 10,149,891 | B2 | 12/2018 | Romero et al. |
| 2002/0146399 | A1 | 10/2002 | Raczek |
| 2005/0281792 | A1 | 12/2005 | Short et al. |

(Continued)

FOREIGN PATENT DOCUMENTS

| | | |
|---|---|---|
| BR | 112015002191-3 A2 | 11/2017 |
| CN | 2013/80051433 | 8/2018 |

(Continued)

OTHER PUBLICATIONS

J. Pallauf and G. Rimbach, Nutritional Significance of Phytic Acid and Phytase, Arch. Anim. Nutr., vol. 50 (1997), pp. 301-319.
C. L. Hofacre, T. Beacorn, S. Collett and G. Mathis, Using Competitve Exclusion, Mannan-Oligosaccharide and Other Intestinal Products To Control Necrotic Enteritis, J.Appl. Poult. Res., vol. 12 (2003), pp. 60-64.
Canada Search Report, 2880419, 19062019.
Canada Search Report, 2880419, 28012020.

(Continued)

*Primary Examiner* — Michelle F. Paguio Frising

(57) ABSTRACT

A method for improving the performance of a subject or for improving digestibility of a raw material in a feed (e.g. nutrient digestibility, such as amino acid digestibility), or for improving nitrogen retention, or for improving dietary phosphorus absorption and retention, or for improving the efficacy of the phytase, or for improving the subject's resistance to necrotic enteritis or for improving feed conversion ratio (FCR) or for improving weight gain in a subject or for improving feed efficiency in a subject or for modulating (e.g. improving) the immune response of the subject or for reducing populations of pathogenic bacteria in the gastrointestinal tract of a subject, or for reducing nutrient excretion in manure, which method comprising administering to a subject at least one direct fed microbial in combination with a phytase, wherein the phytase is administered to the subject at a dosage of more than about 1500 FTU/kg feed.

18 Claims, 8 Drawing Sheets

Specification includes a Sequence Listing.

(56) References Cited

U.S. PATENT DOCUMENTS

| | | |
|---|---|---|
| 2007/0092555 A1 | 4/2007 | Lanahan et al. |
| 2008/0131560 A1 | 6/2008 | Lanahan et al. |
| 2008/0187987 A1 | 8/2008 | Yu et al. |
| 2008/0263688 A1 | 10/2008 | Millan et al. |
| 2010/0143417 A1 | 6/2010 | Skinner et al. |
| 2010/0247706 A1 | 9/2010 | Knap et al. |
| 2010/0284981 A1 | 11/2010 | Baltzley et al. |
| 2011/0086127 A1 | 4/2011 | Webel et al. |
| 2015/0281792 A1 | 10/2015 | Gaydou, II et al. |

FOREIGN PATENT DOCUMENTS

| | | |
|---|---|---|
| MX | 369270 | 11/2019 |
| WO | 1992012645 | 8/1992 |
| WO | 1997016076 | 5/1997 |
| WO | 2004085638 | 10/2004 |
| WO | 2007044968 | 10/2005 |
| WO | 2005123034 | 12/2005 |
| WO | 2006037327 | 4/2006 |
| WO | 2006037328 | 4/2006 |
| WO | 2006038062 | 4/2006 |
| WO | 2006038128 | 4/2006 |
| WO | 2006043178 | 4/2006 |
| WO | 2007112739 | 10/2007 |
| WO | 2008016214 | 2/2008 |
| WO | 2008092901 | 8/2008 |
| WO | 2008097619 | 8/2008 |
| WO | 2009129489 | 10/2009 |
| WO | 2010122532 | 10/2010 |
| WO | 2011117396 | 9/2011 |
| WO | 2012/110777 A2 | 8/2012 |
| WO | WO-2012110778 A2 * | 8/2012 ............. A23K 40/10 |
| WO | 2014/020138 A2 | 2/2014 |

OTHER PUBLICATIONS

Hofacre et al., "Using Competitive Exclusion, Mannan-Oligosaccharide and Other Intestinal Products to Control Necrotic Enteritis", J. Appl. Poult. Res., 2003, vol. 12, pp. 60-64.

* cited by examiner

SEQUENCE LISTING

<160> NUMBER OF SEQ ID NOS: 2

<210> SEQ ID NO 1
<211> LENGTH: 413
<212> TYPE: PRT
<213> ORGANISM: Buttiauxella sp.

<400> SEQUENCE: 1

```
Asn Asp Thr Pro Ala Ser Gly Tyr Gln Val Glu Lys Val Val Ile Leu
  1               5                  10                  15

Ser Arg His Gly Val Arg Ala Pro Thr Lys Met Thr Gln Thr Met Arg
                 20                  25                  30

Asp Val Thr Pro Asn Thr Trp Pro Glu Trp Pro Val Lys Leu Gly Tyr
             35                  40                  45

Ile Thr Pro Arg Gly Glu His Leu Ile Ser Leu Met Gly Gly Phe Tyr
         50                  55                  60

Arg Gln Lys Phe Gln Gln Gln Gly Ile Leu Ser Gln Gly Ser Cys Pro
 65                  70                  75                  80

Thr Pro Asn Ser Ile Tyr Val Trp Thr Asp Val Ala Gln Arg Thr Leu
                 85                  90                  95

Lys Thr Gly Glu Ala Phe Leu Ala Gly Leu Ala Pro Gln Cys Gly Leu
                100                 105                 110

Thr Ile His His Gln Gln Asn Leu Glu Lys Ala Asp Pro Leu Phe His
            115                 120                 125

Pro Val Lys Ala Gly Ile Cys Ser Met Asp Lys Thr Gln Val Gln Gln
        130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335
```

```
Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
            355                 360                 365

Ser Leu Asn Gln Pro Ala Gly Ser Val Gln Leu Lys Ile Pro Gly Cys
            370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 2
<211> LENGTH: 446
<212> TYPE: PRT
<213> ORGANISM: Buttiauxella sp.

<400> SEQUENCE: 2

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
        50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gly Ile Leu Ser Gln Gly Ser Cys
            100                 105                 110

Pro Thr Pro Asn Ser Ile Tyr Val Trp Thr Asp Val Ala Gln Arg Thr
            115                 120                 125

Leu Lys Thr Gly Glu Ala Phe Leu Ala Gly Leu Ala Pro Gln Cys Gly
        130                 135                 140

Leu Thr Ile His His Gln Gln Asn Leu Glu Lys Ala Asp Pro Leu Phe
145                 150                 155                 160

His Pro Val Lys Ala Gly Ile Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Ser Leu Ala Leu Met Asn Thr Thr Leu Asn Phe Ser
            195                 200                 205

Lys Ser Pro Trp Cys Gln Lys His Ser Ala Asp Lys Ser Cys Asp Leu
        210                 215                 220

Gly Leu Ser Met Pro Ser Lys Leu Ser Ile Lys Asp Asn Gly Asn Glu
225                 230                 235                 240

Val Ser Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Leu Leu Leu Lys Leu His Asn Val
            275                 280                 285

Tyr Phe Asp Leu Met Glu Arg Thr Pro Tyr Ile Ala Arg His Lys Gly
```

-continued

```
            290                 295                 300
Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
        370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
                420                 425                 430

Arg Val Val Ser Gln Ser Val Glu Pro Gly Cys Gln Leu Gln
            435                 440                 445
```

FEED ADDITIVE COMPOSITION

CLAIM FOR PRIORITY

This application is a divisional of U.S. patent application Ser. No. 14/866,533, filed Sep. 25, 2015, now U.S. Pat. No. 10,149,891, which is a divisional application of U.S. patent application Ser. No. 13/827,730, filed Mar. 14, 2013, now U.S. Pat. No. 9,179,693, which claims the benefit of Great Britain Application No. 1213801.2, filed on Aug. 3, 2012, each of which is incorporated by reference in its entirety.

INCORPORATION BY REFERENCE OF THE SEQUENCE LISTING

The Sequence Listing submitted in an ASCII text file, in accordance with 37 C.F.R. §§ 1.821(c) and (e), is incorporated herein by reference. The Sequence Listing is provided as a file, titled NB40161USDIV2_SeqList.txt, created on Dec. 4, 2018, which is 7883 bytes in size.

FIELD OF INVENTION

The present invention relates to methods for improving feed compositions using at least one direct fed microbial in combination with a high dose phytase(s), and to a feed additive composition comprising at least one direct fed microbial in combination with a high dose phytase(s). The present invention further relates to uses and kits.

BACKGROUND OF THE INVENTION

Necrotic enteritis is an economically important disease in poultry species. It arises as a result of a pathogenic *Clostridium perfringens* infection, which is often concomitant with coccidiosis infection. In extreme cases, it results in high levels of mortality and at a sub-clinical level results in intestinal damage and detrimental impacts on animal performance. Necrotic enteritis in poultry, and negative effects thereof on performance has primarily been controlled by the use of in-feed antibiotics. However, the ban on the use of in-feed antibiotics as growth promoters and consumer pressure to reduce the use of antibiotic application to meat production animals, has made it more difficult for producers to prevent losses arising from *C. perfringes* and associated sub-clinical or clinical necrotic enteritis. There is therefore an opportunity to offer solutions which limit or prevent the damage caused by *C. perfringens*. One such solution has been to use probiotics to promote a healthy gut microflora and a stable enterological ecosystem. However further benefits have been observed with supplementation with enzymes such as proteases and carbohydrases. Although combinations of DFMs with some enzymes have been contemplated, the interaction between DFMs and enzymes has never been fully understood. The present invention relates to novel specific combinations which surprisingly significantly improve production performance characteristics in animals.

Monogastric animals are known to contain no or negligible amounts of endogenous phytase in the stomach and small intestine, and are therefore dependent on supplemental plant and/or microbial or fungal phytase for hydrolization of phytic acid in the proximal digestive tract (Pallauf, J. and Rimbach, G. *Arch. Anim. Nutr.,* 1997, Vol. 50, pp 301-319). Additional phytase is often added to the feed of monogastric animals, such as poultry and swine feed.

Phytate is the major storage form of phosphorus in cereals and legumes. Through the action of phytase, phytate is generally hydrolysed to give lower inositol-phosphates and inorganic phosphate.

The present invention seeks to overcome some of the problems associated with a reduced beneficial effect of phytase enzymes in animals subject to clinical or sub-clinical necrotic enteritis.

The present invention further seeks to overcome the problems associated with the anti-nutritional properties of phytic acid, particularly in animals subject to clinical or sub-clinical necrotic enteritis, leading to improved availability of nutrients, minerals, vitamins and energy and consequently improved bio-physical characteristics of monogastric animals

SUMMARY OF INVENTION

A seminal finding of the present invention is that the inventors have found that there is an unexpected synergistic effect in the combination of at least one DFM and high levels (>1500 FTU/kg feed) of phytase, which has been shown to improve performance of a subject to a level greater than that of a positive control with low levels of *C. perfringens* and no necrotic enteritis.

The inventors have demonstrated this by considering percentage mortality, body weight gain and FCR for example. These positive effects were completely unexpected.

Without wishing to be bound by theory the inventors believe these affects may be due to a reduced levels of damage to the intestines as a result of pathogen (e.g. *Clostridium perfringens* and/or *Escherichia coli* challenge), compared to the control.

The improved performance of animals may be accounted for through the prevention of the establishment and pathology of harmful bacteria in the gut. In addition it is believed that other beneficial effects of the invention include increased hydrolysis of phytate, which results in increased ileal digestibility of proteins and minerals. In addition to the benefit of increasing nutrient availability to the subject, this can also result in less substrate reaching the hind-gut for fermentation by bacteria, making it harder for the pathogens in the gut to establish. Another benefit of the present invention is the reduced mucin production compared to when phytase is not supplemented. As a result there is a lower level of endogenous losses and again less substrate for fermentation by gut microflora.

In particular, a seminal finding of the present invention is that at least one direct fed microbial (DFM) in combination with high levels (>1500 FTU/kg feed) of phytase has significant beneficial effects on the performance of an animal, including improving one or more of the following: feed conversion ratio (FCR), ability to digest a raw material (e.g. nutrient digestibility, such as amino acid digestibility), nitrogen retention, survival, carcass yield, growth rate, weight gain, feed efficiency, animals resistance to necrotic enteritis, immune response of the subject.

Another surprising effect of the present invention is that it can reduce nutrient excretion in manure (e.g. reduce nitrogen and phosphorus) content of a subject's manure.

In a further aspect of the present invention there is provided a method:
i) for improving the performance of a subject or
ii) for improving digestibility of a raw material in a feed (e.g. nutrient digestibility, such as amino acid digestibility), or iii) for improving phosphorus (e.g. dietary phosphorus) absorption and retention, or iv) for improving the efficacy of the phytase or
v) for improving nitrogen retention, or
vi) for improving the subject's resistance to necrotic enteritis or
vii) for improving feed conversion ratio (FCR) or
viii) for improving weight gain in a subject or
ix) for improving feed efficiency in a subject or
x) for modulating (e.g. improving) the immune response of the subject or
xi) for reducing populations of pathogenic bacteria in the gastrointestinal tract of a subject, or
xii) for reducing nutrient excretion in manure,
which method comprising administering to a subject at least one direct fed microbial in combination with a phytase, wherein the phytase is administered to the subject at a dosage of more than about 1500 FTU/kg feed.

Another aspect of the present invention is the use of at least one direct fed microbial in combination with a phytase, wherein the phytase is used at a dosage of more than about 1500 FTU/kg feed:
i) for improving the performance of a subject or
ii) for improving digestibility of a raw material in a feed (e.g. nutrient digestibility, such as amino acid digestibility) or
iii) for improving nitrogen retention) or
iv) for improving phosphorus (e.g. dietary phosphorus) absorption and retention or
v) for improving the efficacy of the phytase or
vi) for improving the subject's resistance to necrotic enteritis or
vii) for improving feed conversion ratio (FCR) or
viii) for improving weight gain in a subject or
ix) for improving feed efficiency in a subject or
x) for modulating (e.g. improving) the immune response of the subject or
xi) for reducing populations of pathogenic bacteria in the gastrointestinal tract of a subject or
xii) for reducing nutrient excretion in manure.

The present invention yet further provides a feed additive composition comprising at least one direct fed microbial in combination with a phytase, wherein the phytase is present in the feed additive composition:
a. at about 30,000 FTU/g composition or more when dosed in a feed at at least 50 g/metric ton (MT) of feed,
b. at about 20,000 FTU/g composition or more when dosed in a feed at at least 75 g/metric ton (MT) of feed,
c. at about 15,000 FTU/g composition or more when dosed in a feed at at least 100 g/metric ton (MT) of feed,
d. at about 15,000 FTU/g composition or more when dosed in a feed at at least 100 g/metric ton (MT) of feed,
e. at about 10,000 FTU/g composition or more when dosed in a feed at at least 150 g/metric ton (MT) of feed,
f. at about 7,500 FTU/g composition or more when dosed in a feed at at least 200 g/metric ton (MT) of feed,
g. at about 5,000 FTU/g composition or more when dosed in a feed at at least 300 g/metric ton (MT) of feed, and wherein the direct fed microbial is present in the feed additive composition in a range from $2.5 \times 10^3$ CFU DFM: 1 FTU enzyme to $6.7 \times 10^6$ CFU:1 FTU enzyme.

In a further aspect of the present invention, there is provided a kit comprising a feed additive composition according to the present invention and instructions for administration.

In a further aspect the present invention provides a method of preparing a feed additive composition, comprising admixing at least one direct fed microbial with a phytase, such that the dosage of phytase in the composition is:
a. about 30,000 FTU/g composition or more when dosed in a feed at at least 50 g/metric ton (MT) of feed,
b. about 20,000 FTU/g composition or more when dosed in a feed at at least 75 g/metric ton (MT) of feed,
c. about 15,000 FTU/g composition or more when dosed in a feed at at least 100 g/metric ton (MT) of feed,
d. about 15,000 FTU/g composition or more when dosed in a feed at at least 100 g/metric ton (MT) of feed,
e. about 10,000 FTU/g composition or more when dosed in a feed at at least 150 g/metric ton (MT) of feed,
f. about 7,500 FTU/g composition or more when dosed in a feed at at least 200 g/metric ton (MT) of feed,
g. about 5,000 FTU/g composition or more when dosed in a feed at at least 300 g/metric ton (MT) of feed,
and the dosage of the direct fed microbial in the feed additive composition in a range from $2.5 \times 10^3$ CFU DFM: 1 FTU enzyme to $6.7 \times 10^6$ CFU:1 FTU enzyme, and (optionally) packaging.

In a further aspect the present invention provides a feed comprising a feed additive composition according to the present invention.

The present invention yet further provides a method of preparing a feedstuff comprising admixing a feed component with a feed additive composition according to the present invention.

In another aspect, the present invention provides a premix comprising a feed additive composition comprising at least one direct fed microbial in combination with a phytase, wherein the phytase is present in the premix at:
a. about 30,000 FTU/g composition or more when dosed in a feed at at least 50 g/metric ton (MT) of feed,
b. about 20,000 FTU/g composition or more when dosed in a feed at at least 75 g/metric ton (MT) of feed,
c. about 15,000 FTU/g composition or more when dosed in a feed at at least 100 g/metric ton (MT) of feed,
d. about 15,000 FTU/g composition or more when dosed in a feed at at least 100 g/metric ton (MT) of feed,
e. about 10,000 FTU/g composition or more when dosed in a feed at at least 150 g/metric ton (MT) of feed,
f. about 7,500 FTU/g composition or more when dosed in a feed at at least 200 g/metric ton (MT) of feed,
g. about 5,000 FTU/g composition or more when dosed in a feed at at least 300 g/metric ton (MT) of feed,
and the direct fed microbial is present in the premix in a range from $2.5 \times 10^3$ CFU DFM: 1 FTU enzyme to $6.7 \times 10^6$ CFU:1 FTU enzyme, and at least one mineral and/or at least one vitamin.

The present invention also provides a feed additive composition according to the present invention or a premix according to the present invention or a feed comprising a feed additive composition (or premix) according to the present invention for preventing and/or treating coccidiosis and/or necrotic enteritis in a subject.

In a yet further aspect of the present invention there is provided a method of preventing and/or treating necrotic enteritis and/or coccidiosis wherein an effective amount of a feed additive composition according to the present invention or a premix according to the present invention or a feed comprising a feed additive composition (or premix) according to the present invention is administered to a subject.

In one broad aspect the present invention yet further provides a method or use:
i) for improving digestibility of a raw material in a feed (e.g. nutrient digestibility, such as amino acid digestibility), or
ii) for improving the performance of a subject or
iii) for improving phosphorus (e.g. dietary phosphorus) absorption and retention, or
iv) for improving the efficacy of the phytase or
v) for improving nitrogen retention, or
vi) for improving the subject's resistance to necrotic enteritis or
vii) for improving feed conversion ratio (FCR) or
viii) for improving weight gain in a subject or
ix) for improving feed efficiency in a subject or
x) for modulating (e.g. improving) the immune response of the subject or
xi) for reducing populations of pathogenic bacteria in the gastrointestinal tract of a subject, or
xii) for reducing nutrient excretion in manure,
which method comprising administering to a subject a high dosage phosphate together with a compound which reduces the pH in the subjects gastrointestinal tract (GIT). In this broad aspect, suitably the compound may be an organic acid, an essential oil or an antibiotic. The organic acid may be selected from one or more of the group consisting of: citric acid, fumaric acid, formic acid, propionic acid, lactic acid and benzoic acid. The antibiotic may be selected from one or more of the group consisting of: tetracycline, chlortetracycline, oxytetracycline, oleandomycin, spiramycin, virginiamycin, bacitracin zinc, flavophospholipol, avilamycin and avoparcin. The essential oil (or plant extract) may be selected from one or more of the group consisting of cinnemaldehyde, thymol, carvacrol, capsaicin, euganol and alicin.

DETAILED DESCRIPTION OF THE INVENTION

Figure 1:
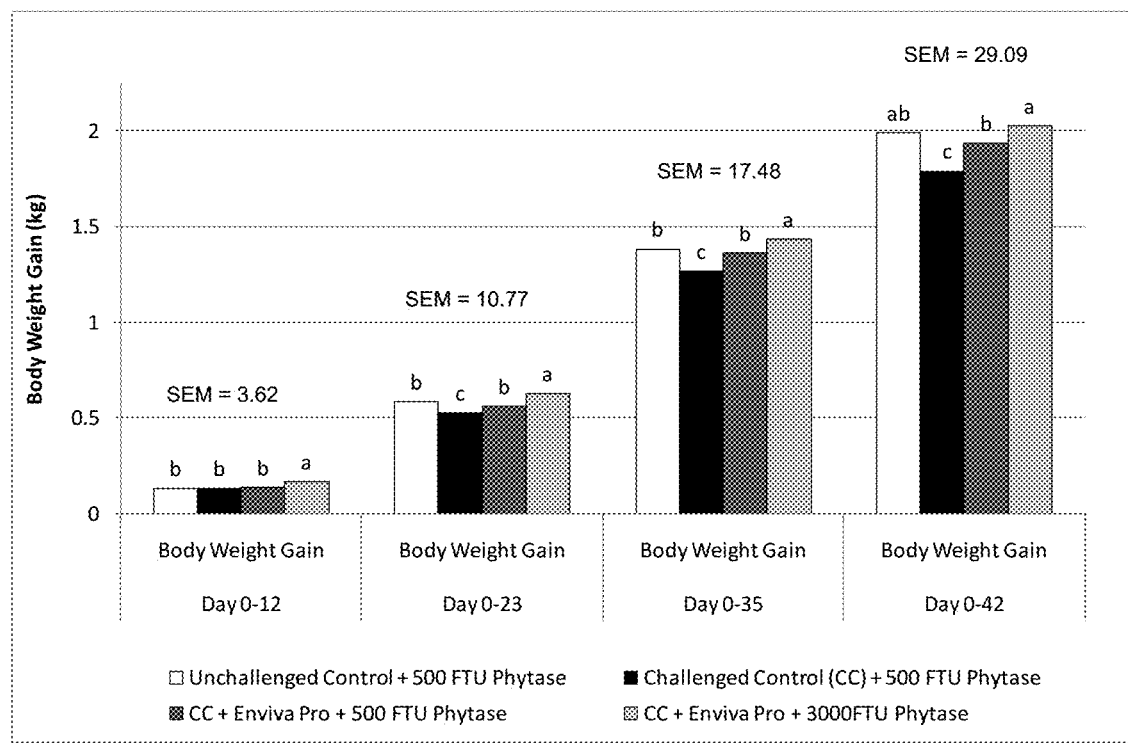
FIG. 1 shows the effect of supplementation of EnvivaPro and a High Phytase Dose (3000 FTU/kg) on Body Weight Gain of broilers raised to 42 days under a Necrotic Enteritis challenge.
Figure 2:
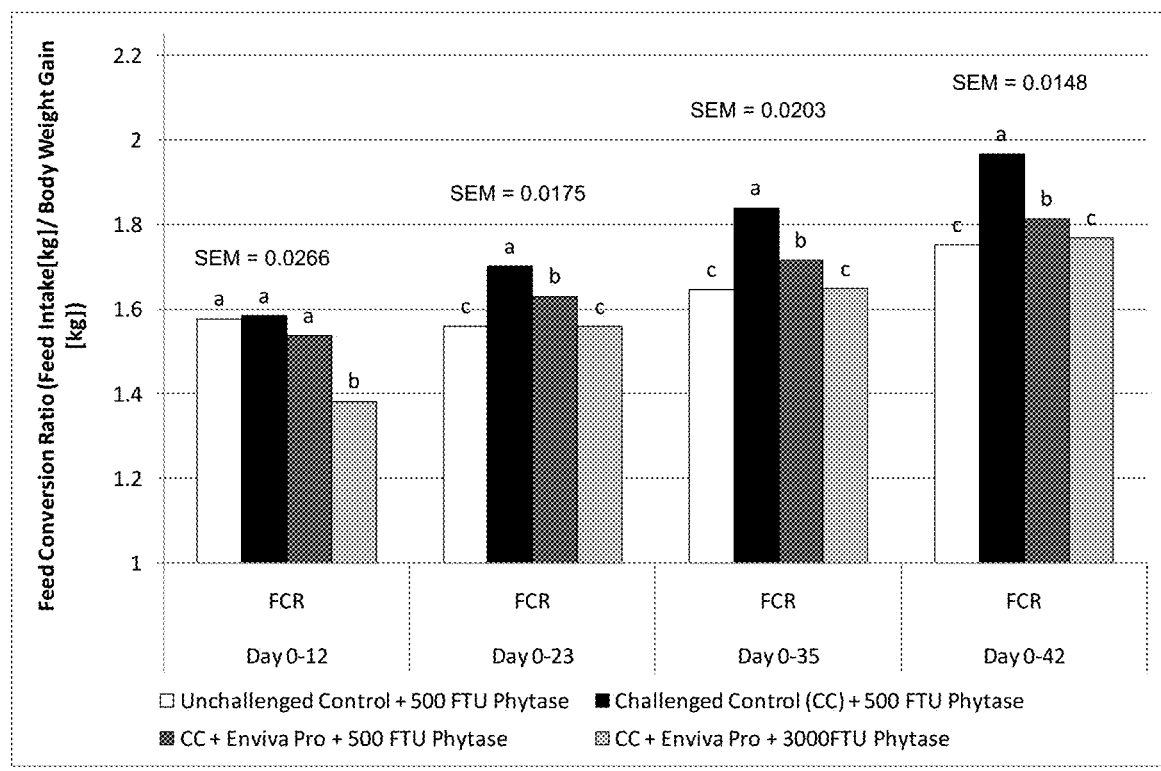
FIG. 2 shows the effect of supplementation of Enviva Pro and a High Phytase Dose (3000 FTU/kg) on FCR of broilers raised to 42 days under a Necrotic Enteritis challenge.
Figure 3:
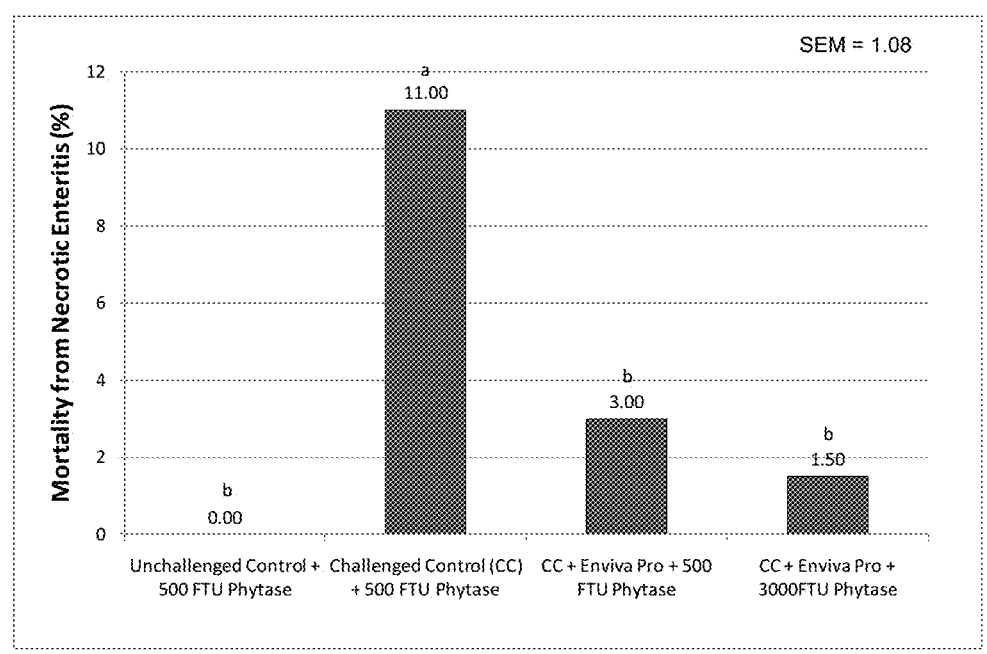
FIG. 3 shows the effect of Enviva Pro and High Phytase Dose (3000 FTU/kg) on mortality as a result of a Necrotic Enteritis challenge.
Figure 4:
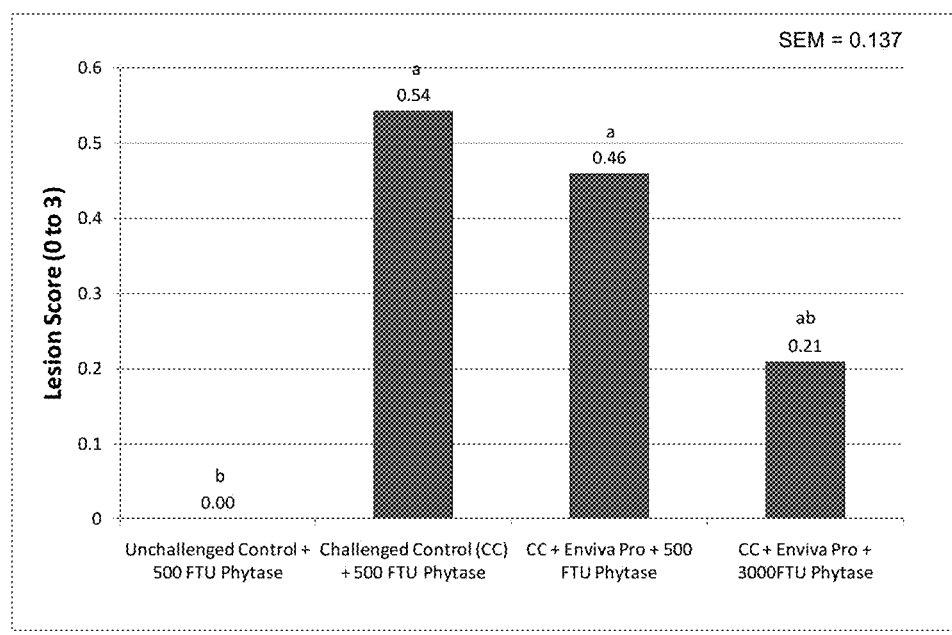
FIG. 4 shows the effect of Enviva Pro and High Phytase Dose (3000 FTU/kg) on the severity of intestinal damage due to a Necrotic Enteritis challenge.

Preferably each of the enzymes used in the present invention are exogenous to the DFM. In other words the enzymes are preferably added to or admixed with the DFM.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation.

The term "protein", as used herein, includes proteins, polypeptides, and peptides.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" includes a plurality of such candidate agents and reference to "the feed" includes reference to one or more feeds and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

The enzymes for use in the present invention can be produced either by solid or submerged culture, including batch, fed-batch and continuous-flow processes. Culturing is accomplished in a growth medium comprising an aqueous mineral salts medium, organic growth factors, the carbon and energy source material, molecular oxygen, and, of course, a starting inoculum of one or more particular microorganism species to be employed.

The direct fed microbial (DFM) for use in the present invention may be an antipathogen direct fed microbial. The term "antipathogen DFM" as used herein means a DFM that inhibits (e.g. decreases or prevents) intestinal establishment of pathogenic microorganism (such as *Clostridium perfringens* and/or *E. coli* and/or *Salmonella* spp and/or *Campylobacter* spp., preferably *Clostridium perfringens* and/or *E. coli*).

The "DFM ASSAY" taught hereinbelow may be used to determine whether the DFM is an antipathogen DFM.

In one embodiment the DFM for use in the present invention is selected as an inhibitory strain (or an antipathogen DFM) when assessed with the "DFM ASSAY" taught herein.

Suitably the DFM for use in the present invention may inhibit one (or more) of the following pathogens: *Clostridium* spp, such as *Clostridium perfringens* and/or *Clostridium difficile*, and/or *E. coli* and/or *Salmonella* spp and/or *Campylobacter* spp, preferably at least one (or more) of the following pathogens: *Clostridium* spp, such as *Clostridium perfringens* and/or *Clostridium difficile*, and/or *E. coli*.

In one embodiment the DFM for use in the present invention may inhibit one (or more) of the following pathogens: *Clostridium perfringens* and/or *Clostridium difficile* and/or *E. coli*, preferably *Clostridium perfringens* and/or *Clostridium difficile*, more preferably *Clostridium perfringens*.

In one embodiment the subject may be challenged by a pathogen, such as one or more of the following pathogens: *Clostridium* spp, such as *Clostridium perfringens* and/or *Clostridium difficile*, and/or *E. coli* and/or *Salmonella* spp and/or *Campylobacter* spp.

In one embodiment the subject may be challenged by *Clostridium perfringens* and/or *E. coli*. The DFM for use in the present invention is suitably a viable bacterium.

The present invention relates to high phytase dosages.

Conventionally phytase is dosed in the region of about 500 FTU/kg feed e.g. for broilers and turkeys, and as is conventionally doses in the region of about 300 FTU/kg feed for laying hens for example.

In contrast in the present invention the phytase is dosed in (or with) the feedstuff at a level of at least 1500 FTU/kg feed, suitably at least 2000 FTU/kg feed, suitably at least 3000 FTU/kg feed, suitably at least 5000 FTU/kg feed, such as at least 10000 FTU/kg feed.

As will be understood by one skilled in the art, the level of phytase in the feed additive composition must be sufficient to allow the phytase to be dosed in the feedstuff at a level of at least 1500 FTU/kg feed, suitably at least 2000 FTU/kg feed, suitably at least 3000 FTU/kg feed, suitably at least 5000 FTU/kg feed, such as at least 10000 FTU/kg feed.

The present inventors have found that significant benefits can be obtained by administering high phytase levels in combination with DFMs. In contrast, increasing the dose of phytase alone causes no significant benefits (e.g. no significant improvements in feed conversion ratios etc.). In sharp contradistinction when the dose of phytase is increased in combination with at least one DFM (particularly at least antipathogen DFM)—then significant and unexpected benefits are observed. This was completely unexpected.

Suitably the DFM for use in the present invention is a mixture of at least two DFMs, suitably at least three DFMs.

In one embodiment the DFM for use in the present invention comprises (or consists essentially of or consists of) a bacterium from one or more of the following genera: *Bacillus, Enterococcus, Pediococcus, Saccharomyces, Bifidobacterium, Lactobacillus, Lactococcus, Aspergillus* and combinations thereof.

The DFM for use in the present invention may comprise (or consist essentially of or consist of) a bacterium from one or more of the following species: *Bacillus subtilis, Bacillus licheniformis, Bacillus amyloliquefaciens, Bacillus cereus, Enterococcus faecium, Pediococcus acidilactici, Saccharomyces cerevisiae, Bifidobacterium animalis* spp *animalis, Lactobacillus reuteri, Lactobacillus rhamnosus, Lactobacillus salivarius* ssp *salivarius, Lactobacillus farciminis, Lactococcus lactis, Clostridium butyricum, Aspergillus oryzae* and combinations thereof.

The DFM for use in the present invention may comprise (or consist essentially or consist of) one or more of the following strains: *Bacillus subtilis* BS18 (NRRL B-50633), *Bacillus subtilis* BS278 (NRRL 50634), *Bacillus subtilis* 4-7 d (NRRL B-50505), *Bacillus subtilis* 3-5 h (NRRL B-50507), *Bacillus subtilis* AGTP BS3BP5 (NRRL B-50510), *Bacillus subtilis* BS918 (NRRL B-50508), *Bacillus subtilis* AGTP BS1013 (NRRL-50509), *B. subtilis* AGTP 944 (NRRL B-50548), *Bacillus subtilis* AGTP BS442 (NRRL B-50542), *B. subtilis* AGTP BS1069 (NRRL B-50544), *B. subtilis* AGTP BS521 (NRRL B-50545), *B. subtilis* BS2084 (NRRL B-50013), *B. subtilis* LSSA01 (NRRL B-50104), *B. subtilis* B27 (NRRL B-50105), *B. subtilis* 3A-P4 (PTA-6506), *Bacillus subtilis* 15A-P4 (PTA-6507), *B. subtilis* 22C-P1 (PTA-6508), *B. subtilis* BL21 (NRRL B-50134), *Bacillus licheniformis* BL21 (NRRL B-50134), *Bacillus licheniformis* 3-12a (NRRL B-50504), *Bacillus licheniformis* 4-2a (NRRL B-50506), *Bacillus licheniformis* 842 (NRRL B-50516), *Propionibacterium acidipropionici* P261 (NRRL B-50131), *Propionibacterium acidipropionici* P179 (NRRL B-50133), *Propionibacterium acidipropionici* P169 (PTA 5271), *Propionibacterium acidipropionici* P170 (PTA 5272), *Propionibacterium jensenii* P63 (NRRL B-30979), *Propionibacterium jensenii* P195

(NRRL B-50132), *Lactococcus lactis* ID7 (PTA 6103), *Lactococcus lactis* JD19 (PTA 6104), *Lactobacillus acidophilus* A2020 (NRRL B-30977), *Lactobacillus acidophilus* A4000 h (NRRL B-30978), *Lactobacillus acidophilus* PIBc6 (NRRL B-50103), *Lactobacillus brevis* LBR 1000 (NRRL B-30982), *Lactobacillus casei* LC222 (NRRL B-30983), *Lactobacillus johnsonii* PLCB6 (NRRL B-50518), *Lactobacillus salivarius* o246i33w (NRRL B-50102), *Lactobacillus brevis* AJ25 (PTA-6099), *Lactobacillus brevis* HE17 (PTA-6100), *Lactobacillus brevis* 1E-1 (PTA-6509), *Lactobacillus lactis* C115 (PTA-6101), *Lactobacillus lactis* DJ6 (PTA-6102), *Lactobacillus rhamnosus* (CNCM 1-3698), *Lactobacillus farciminis* (CNCM 1-3699), *Enterococcus faecium* EF141 (EN-1) (NRRL B-30981), *Enterococcus faecium* 2-1 d (NRRL B-50519), *Pediococcus acidilactici* PlJe3 (NRRL B-50101), *Pediococcus acidilactici* o246e42 (NRRL B-50171) and combinations thereof.

The DFM for use in the present invention may comprise more than more, suitably more than two, suitably at least three *Bacillus* spp.

The DFM for use in the present invention may comprise (or consist essentially or consist of) one or more of the following strains: *Bacillus subtilis* strains 3A-P4 (PTA-6506); 15A-P4 (PTA-6507); 22C-P1 (PTA-6508); 2084 (NRRL B-500130); LSSA01 (NRRL-B-50104); BS27 (NRRL B-50105); BS 18 (NRRL B-50633); and BS 278 (NRRL B-50634) or combinations thereof.

In one embodiment the DFM for use in the present invention may comprise (or consist essentially or consist of) one or more of the following strains: *Bacillus subtilis* strains 15A-P4 (PTA-6507); 2084 (NRRL B-500130); LSSA01 (NRRL-B-50104).

In one embodiment the phytase for use in the present invention is a 6-phytase or a 3-phytase, preferably a 6-phytase.

In one embodiment the phytase for use in the present invention may be selected from one or more of the groups consisting of: an *E. coli* phytase or a *Buttiauxella* phytase or a *Citrobacter* phytase or a *Hafnia* phytase or an *Aspergillus* phytase or a *Penicillium* phytase or a *Trichoderma* phytase or an *E. coli* phytase or a *Hansenula* phytase, or combination thereof.

In one embodiment the phytase for use in the present invention may be 6-phytase from one or more of the following: *E. coli, Buttiauxella* spp. or *Citrobacter* spp, e.g. *Citrobacter* braakii, including combinations thereof.

Suitably the phytase for use in the present invention may be one or more PhyzymeXP™, AxtraPhy™, or Ronozyme HiPhos™, or Quantum™ or Quantum Blue™.

Suitably the phytase may be a mixture or more than one phytase, such as at least 2 or at least 3 phytases.

In one embodiment preferably the phytase for use in the present invention is active at low pH (e.g. is active at between pH2 and pH5.5).

In one embodiment preferably the phytase for use in the present invention has an optimum pH at low pH (e.g. has an optimum pH in the range of pH2 and pH5.5).

In one embodiment a clinical or subclinical intestinal disease challenge is present in the subject.

In one embodiment the clinical or subclinical intestinal disease challenge may be caused by any pathogen or any pathogenic bacteria, such as *Clostridium perfringens* or *E. coli*.

In one embodiment the dosage of the direct fed microbial in the feed additive composition may be in a range from $3.8 \times 10^3$ CFU DFM: 1 FTU enzyme to $2.0 \times 10^5$ CFU:1 FTU enzyme.

Direct Fed Microbial (DFM)

The term "microbial" herein is used interchangeably with "microorganism".

Preferably the DFM comprises a viable microorganism. Preferably the DFM comprises a viable bacterium or a viable yeast or a viable fungi.

Preferably the DFM comprises a viable bacteria.

The term "viable microorganism" means a microorganism which is metabolically active or able to differentiate.

In one embodiment the DFM may be a spore forming bacterium and hence the term DFM may be comprised of or contain spores, e.g. bacterial spores. Therefore in one embodiment the term "viable microorganism" as used herein may include microbial spores, such as endospores or conidia.

In another embodiment the DFM in the feed additive composition according to the present invention is not comprised of or does not contain microbial spores, e.g. endospores or conidia.

The microorganism may be a naturally occurring microorganism or it may be a transformed microorganism. The microorganism may also be a combination of suitable microorganisms. In some aspects, the DFM according to the present invention may be one or more of the following: a bacterium, a yeast, a fungi.

Preferably the DFM according to the present invention is a probiotic microorganism.

In the present invention, the term direct fed microbial (DFM) encompasses direct fed bacteria, direct fed yeast, direct fed fungi and combinations thereof.

Preferably the DFM is a direct fed bacterium.

Preferably the DFM is a combination comprising two or more bacteria, e.g. three or more or four or more; or the DFM is a combination comprising two or more bacterial strains, e.g. three or more or four or more.

Preferably the bacterium or bacteria is or are isolated.

Suitably the DFM may comprise a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* and combinations thereof.

In one embodiment the DFM may be selected from the following *Bacillus* spp: *Bacillus subtilis, Bacillus cereus, Bacillus licheniformis, Bacillus amyloliquefaciens* and *Bacillus pumilus*.

In one embodiment the DFM may be a *Bacillus* strain.

In one embodiment the DFM may be selected from the group consisting of: *Bacillus subtilis* BS18 (NRRL B-50633), *Bacillus subtilis* BS278 (NRRL 50634), *Bacillus subtilis* 4-7 d (NRRL B-50505), *Bacillus subtilis* 3-5 h (NRRL B-50507), *Bacillus subtilis* AGTP BS3BP5 (NRRL B-50510), *Bacillus subtilis* BS918 (NRRL B-50508), *Bacillus subtilis* AGTP BS1013 (NRRL-50509), *B. subtilis* AGTP 944 (NRRL B-50548), *Bacillus subtilis* AGTP BS442 (NRRL B-50542), *B. subtilis* AGTP BS1069 (NRRL B-50544), *B. subtilis* AGTP BS521 (NRRL B-50545), *B. subtilis* BS2084 (NRRL B-50013), *B. subtilis* LSSA01 (NRRL B-50104), *B. subtilis* B27 (NRRL B-50105), *B. subtilis* 3A-P4 (PTA-6506), *Bacillus subtilis* 15A-P4 (PTA-6507), *B. subtilis* 22C-P1 (PTA-6508), *B. subtilis* BL21 (NRRL B-50134) and combinations thereof.

For the avoidance of doubt, *B. subtilis* LSSA01 (NRRL B-50104) is sometimes referred to as strain BSB.

In one embodiment the DFM may be selected from the group consisting of: *Bacillus pumilus* strain AGTP BS 1068 (NRRL B-50543) or *B. pumilus* KX11-1 (NRRL B-50546) and combinations thereof.

In one embodiment the DFM may be selected from the group consisting of:
*Bacillus licheniformis* BL21 (NRRL B-50134), *Bacillus licheniformis* 3-12a (NRRL B-50504),
*Bacillus licheniformis* 4-2a (NRRL B-50506) and *Bacillus licheniformis* 842 (NRRL B-50516).

In one embodiment the DFM may be a combination comprising two or more *Bacillus* strains. In one embodiment the DFM may be a combination of two or more the *Bacillus subtilis* strains 3A-P4 (PTA-6506); 15A-P4 (PTA-6507); 22C-P1 (PTA-6508); 2084 (NRRL B-500130); LSSA01 (NRRL-B-50104); BS27 (NRRL B-50105); BS 18 (NRRL B-50633); and BS 278 (NRRL B-50634).

In a preferred embodiment the DFM may comprise (or consist essentially of or consist of) one of the following combinations:

*B. subtilis* LSSA01 (NRRL B-50104)+*Bacillus subtilis* BS18 (NRRL B-50633)+*B. subtilis* 22C-P1 (PTA-6508); or

*B. subtilis* LSSA01 (NRRL B-50104)+*B. subtilis* 3A-P4 (PTA-6506)+*B. subtilis* BS2084 (NRRL B-50013); or

*B. subtilis* LSSA01 (NRRL B-50104)+*B. subtilis* 3A-P4 (PTA-6506)+*B. subtilis* BS2084 (NRRL B-50013)+*Bacillus subtilis* 15A-P4 (PTA-6507); or

*B. subtilis* 3A-P4 (PTA-6506)+*B. subtilis* 22C-P1 (PTA-6508)+*B. subtilis* BS2084 (NRRL B-50013); or

*B. subtilis* LSSA01 (NRRL B-50104)+*Bacillus subtilis* 15A-P4 (PTA-6507)+*B. subtilis* BS2084 (NRRL B-50013); or

*B. subtilis* 3A-P4 (PTA-6506)+*Bacillus subtilis* BS18 (NRRL B-50633)+*B. subtilis* 22C-P1 (PTA-6508); or

*B. subtilis* 3A-P4 (PTA-6506)+*B. subtilis* BS2084 (NRRL B-50013)+*Bacillus subtilis* BS278 (NRRL 50634).

Strains 3A-P4 (PTA-6506), 15A-P4 (PTA-6507) and 22C-P1 (PTA-6508) are publically available from American Type Culture Collection (ATCC).

Strains 2084 (NRRL B-500130); LSSA01 (NRRL-B-50104); BS27 (NRRL B-50105) are publically available from the Agricultural Research Service Culture Collection (NRRL). Strain *Bacillus subtilis* LSSA01 is sometimes referred to as *B. subtilis* 8.

These strains are taught in U.S. Pat. No. 7,754,469 B2.

Danisco USA Inc. of W227 N752 Westmound Dr. Waukesha, Wis. 53186, USA also deposited under the Budapest Treaty the following deposits with the Agricultural Research Service Culture Collection (NRRL) at 1815 North University Street, Peoria, Ill. 61604, United States of America with the dates of the original deposits and accession numbers detailed below:

| | | |
|---|---|---|
| *Bacillus licheniformis* 3-12a | NRRL B-50504 | 13 May 2011 |
| *Bacillus licheniformis* 4-2a | NRRL B-50506 | 13 May 2011 |
| *Bacillus licheniformis* BL842 | NRRL B-50516 | 20 May 2011 |
| *Bacillus pumilus* AGTP KXII-1 | NRRL B-50546 | 5 Aug. 2011 |
| *Bacillus pumilus* AGTP BS1068 | NRRL B-50543 | 4 Aug. 2011 |
| *Bacillus subtilis* BS18 | NRRL B-50633 | 9 Jan. 2012 |
| *Bacillus subtilis* BS278 | NRRL B-50634 | 9 Jan. 2012 |
| *Bacillus subtilis* 4-7 d | NRRL B-50505 | 13 May 2011 |
| *Bacillus subtilis* 3-5 h | NRRL B-50507 | 13 May 2011 |
| *Bacillus subtilis* AGTP BS3BP5 | NRRL B-50510 | 13 May 2011 |
| *Bacillus subtilis* AGTP BS918 | NRRL B-50508 | 13 May 2011 |
| *Bacillus subtilis* AGTP BS1013 | NRRL B-50509 | 13 May 2011 |
| *Bacillus subtilis* AGTP 944 | NRRL B-50548 | 11 Aug. 2011 |
| *Bacillus subtilis* AGTP BS442 | NRRL B-50542 | 4 Aug. 2011 |
| *Bacillus subtilis* AGTP BS1069 | NRRL B-50544 | 4 Aug. 2011 |
| *Bacillus subtilis* AGTP BS521 | NRRL B-50545 | 4 Aug. 2011 |

Danisco USA Inc. of W227 N752 Westmound Dr. Waukesha, Wis. 53186, USA authorises DuPont Nutrition Biosciences ApS of Langebrogade 1, PO Box 17, DK-1001, Copenhagen K, Denmark to refer to all of these deposited biological materials in this patent application and have given unreserved and irrevocable consent to the deposited material being made available to the public.

In some embodiments the DFM may be a combination comprising the *Bacillus subtilis* strains as detailed in the table below:

| *B. subtilis* strain | Bs 2084 | Bs 8 (LSSAO1) | Bs 3A-P4 | Bs 15A-P4 | Bs 278 | Bs 18 | Bs 22C-P1 |
|---|---|---|---|---|---|---|---|
| DFM Combination comprises | X | X | X | X | | | |
| | X | X | X | | | | |
| | X | X | | | | X | |
| | X | X | | X | | | |
| | X | | | X | X | | |
| | | X | X | X | | | |
| | X | X | | | | X | |
| | | | X | X | | | X |
| | X | X | | | X | | |

In one embodiment the DFM may be selected from *Lactococcus* spp.

In one embodiment the DFM may be selected from one or more of the following *Lactococcus* spp: *Lactococcus cremoris* and *Lactococcus lactis* and combinations thereof.

In one embodiment the DFM may be selected from the group consisting of the following strains or a combination thereof:

| | |
|---|---|
| *Lactococcus lactis* ID7 | PTA 6103 |
| *Lactococcus lactis* JD19 | PTA 6104 |

In one embodiment the DFM may be a *Lactobacillus* spp.

In one embodiment the DFM may be selected from the following *Lactobacillus* spp: *Lactobacillus buchneri, Lactobacillus acidophilus, Lactobacillus casei, Lactobacillus kefiri, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sakei, Lactobacillus reuteri, Lactobacillus fermentum, Lactobacillus farciminis, Lactobacillus lactis, Lactobacillus delbreuckii, Lactobacillus plantarum, Lactobacillus paraplantarum, Lactobacillus farciminis, Lactobacillus rhamnosus, Lactobacillus crispatus, Lactobacillus gasseri, Lactobacillus johnsonii* and *Lactobacillus jensenii*, and combinations of any thereof.

In one embodiment the DFM may be selected from the group consisting of the following strains or a combination thereof:

| | |
|---|---|
| Lactobacillus acidophilus A2020 | NRRL B-30977 |
| Lactobacillus acidophilus A4000h | NRRL B-30978 |
| Lactobacillus acidophilus PIBc6 | NRRL B-50103 |
| Lactobacillus brevis LBR 1000 | NRRL B-30982 |
| Lactobacillus casei LC222 | NRRL B-30983 |
| Lactobacillus johnsonii PLCB6 | NRRL B-50518 |
| Lactobacillus salivarius o246i33w | NRRL B-50102 |
| Lactobacillus brevis AJ25 | PTA-6099 |
| Lactobacillus brevis HE17 | PTA-6100 |
| Lactobacillus brevis 1E-1 | PTA-6509 |
| Lactobacillus lactis CI15 | PTA-6101 |
| Lactobacillus lactis DJ6 | PTA-6102 |
| Lactobacillus rhamnosus | CNCM I-3698 |
| Lactobacillus farciminis | CNCM I-3699 |

In one embodiment the DFM may be selected from one or more of the following strains: *Lactobacillus rhamnosus* CNCM-I-3698 and *Lactobacillus* farciminis CNCM-I-3699. These strains were deposited at the Collection Nationale de Cultures de Microorganims (CNCM) 25, Rue due Docteur Roux, F75724 Paris Cedex 15, France on 8 Dec. 2006 by Sorbial, Route de Spay 72700 Allonnes, France and all right, title and interest in the deposits were subsequently transferred to Danisco France SAS of 20, Rue de Brunel, 75017 Paris, France.

Danisco France SAS has authorised DuPont Nutrition Biosciences ApS of Langebrogade 1, PO Box 17, DK-1001, Copenhagen K, Denmark to refer to these deposited biological materials in this patent application and have given unreserved and irrevocable consent to the deposited material being made available to the public.

In one embodiment the DFM may be the Sorbiflore® product available from Danisco Animal Nutrition.

In one embodiment the DFM may be from the genus *Pediococcus*.

In one embodiment the DFM may be from the following *Pediococcus* species: *Pediococcus acidilactici*, such as one or more of the following *P. acidilactici* strains PlJe3 (NRRL B-50101) or o246e42 (NRRL B-50171).

In one embodiment the DFM may be selected from the following Bifidobacteria spp: *Bifidobacterium lactis, Bifidobacterium bifidium, Bifidobacterium longum, Bifidobacterium animalis, Bifidobacterium breve, Bifidobacterium infantis, Bifidobacterium catenulatum, Bifidobacterium pseudocatenulatum, Bifidobacterium adolescentis*, and *Bifidobacterium angulatum*, and combinations of any thereof.

In one embodiment the DFM may be an *Enterococcus* spp.

In one embodiment the DFM may be from the species *Entercoccus faecium*.

In one embodiment the DFM may be selected from the group consisting of *Enterococcus faecium* EF141 (EN-1) (NRRL B-30981), *Enterococcus faecium* 2-1 d (NRRL B-50519) and combinations thereof.

In one embodiment the DFM may be from the genus *Proprionbacterium*.

In one embodiment the DFM may be selected from the group consisting of the following *Proprionbacterium* species or a combination thereof: *Proprionbacterium acidipropionici* and *Propionibacterium jensenii*.

In one embodiment the DFM may selected from the group consisting of the following *Proprionbacterium* strains or combinations thereof:

| | |
|---|---|
| Propionibacterium acidipropionici P261 | NRRL B-50131 |
| Propionibacterium acidipropionici P179 | NRRL B-50133 |
| Propionibacterium acidipropionici P169 | PTA 5271 |
| Propionibacterium acidipropionici P170 | PTA 5272 |
| Propionibacterium jensenii P63 | NRRL B-30979 |
| Propionibacterium jensenii P195 | NRRL B-50132 |

Suitably the DFM may comprise a bacterium from one or more of the following species: *Bacillus subtilis, Bacillus licheniformis, Bacillus amyloliquefaciens, Enterococcus faecium, Enterococcus* spp, and *Pediococcus* spp, *Lactobacillus* spp, *Bifidobacterium* spp, *Lactobacillus acidophilus, Pediococsus acidilactici, Lactococcus lactis, Bifidobacterium bifidum, Bacillus subtilis, Propionibacterium thoenii, Lactobacillus farciminis, Lactobacillus rhamnosus, Megasphaera elsdenii, Clostridium butyricum, Bifidobacterium animalis* ssp. *animalis, Lactobacillus reuteri, Bacillus cereus, Lactobacillus salivarius* ssp. *Salivarius*, Propionibacteria sp and combinations thereof.

The direct fed bacterium used in the present invention may be of the same type (genus, species and strain) or may comprise a mixture of genera, species and/or strains.

Suitably the DFM according to the present invention may be one or more of the products or the microorganisms contained in those products as in the Table below:

| Product Name | Company | Microorganism(s) | Symbiotic ingredients |
|---|---|---|---|
| Enviva Pro ®. (formerly known as Avicorr ®) | Danisco A/S | *Bacillus subtilis* strain 2084 Accession No. NRRI B-50013, *Bacillus subtilis* strain LSSAO1 Accession No. NRRL B-50104 and *Bacillus subtilis* strain 15A-P4 ATCC Accession No. PTA-6507 | |
| Calsporin ® | Calpis - Japan | *Bacillus subtilis* Strain C3102 | |
| Clostat ® | Kemin Industries Inc. | *Bacillus subtilis* Strain PB6 | |
| Cylactin ® | DSM | *Enterococcus faecium* NCIMB 10415 (SF68) | |
| Gallipro ® & GalliproMax ® | Chr. Hansen A/S | *Bacillus subtilis* Strain C3102 | |
| Gallipro ®Tect ® | Chr. Hansen A/S | *Bacillus licheniformis* | |
| Poultry star ® | Biomin, Inc | *Enterococcus* and *Pediococcus* | Fructo-oligosaccharides |
| Protexin ® | Protexin Int | *Lactobacillus, Bifidobacterium* and another | |

-continued

| Product Name | Company | Microorganism(s) | Symbiotic ingredients |
|---|---|---|---|
| Proflora ® | Alpharma Inc. | *Bacillus subtilis* strain QST 713 | β-Mos β-mannan oligosaccharides and β-glucans |
| Ecobiol ® & Ecobiol ® Plus | Norel S.A. | *Bacillus amyloliquefaciens* CECT-5940 | |
| Fortiflora ® | | *Enterococcus faecium* SF68 | |
| BioPlus2B ® | DSM | *Bacillus subtilis* and *Bacillus licheniformis* | |
| Lactiferm ® | Chr. Hansen | Lactic acid bacteria 7 *Enterococcus faecium* | |
| CSI ® | Danisco A/S | *Bacillus* strain | |
| Yea-Sacc ® | Alltech | *Saccharomyces cerevisiae* | |
| Biomin IMB52 ® | Biomin | *Enterococcus faecium* | |
| Biomin C5 ® | Biomin | *Pediococcus acidilactici*, *Enterococcus faecium*, *Bifidobacterium animalis* ssp. *animalis*, *Lactobacillus reuteri* *Lactobacillus salivarius* ssp. *salivarius* | |
| Biacton ® | ChemVet | *Lactobacillus farciminis* | |
| Oralin E1707 ® | Chevita GmBH | *Enterococcus faecium* | |
| Probios-pioneer PDFM ® | Chr Hansen | *Enterococcus faecium* (2 strains) *Lactococcus lactis* DSM 11037 | |
| Sorbiflore ® | Danisco Animal Nutrition | *Lactobacillus rhamnosus* and *Lactobacillus farciminis* | |
| Animavit ® | KRKA | *Bacillus subtilis* | |
| Bonvital ® | Lactosan GmbH | *Enterococcus faecium* | |
| Levucell SB 20 ® | Lallemand | *Saccharomyces cerevisiae* | |
| Levucell SC 0 & SC10 ® ME | Lallemand | *Saccharomyces cerevisiae* | |
| Bactocell | Lallemand | *Pediococcus acidilacti* | |
| ActiSaf ® (formerly BioSaf ®) | Le Saffre | *Saccharomyces cerevisiae* | |
| Actisaf ® SC47 | Le Saffre | *Saccharomyces cerevisiae* NCYC Sc47 | |
| Miya-Gold ® | Miyarisan Pharma | *Clostridium butyricum* | |
| Fecinor and Fecinor Plus ® | Norel S.A | *Enterococcus faecium* | |
| InteSwine ® | ntegro Gida ve Ticaret AS represented by RM Associates Ltd | *Saccharomyces cerevisiae* NCYC R-625 | |
| BioSprint ® | ProSol SpA | *Saccharomyces cerevisia* | |
| Provita ® | Provita | *Enterococcus faecium* and *Lactobacillus rhamnosus* | |
| PepSoyGen-C ® | Regal BV (Nutraferma) | *Bacillus subtilis* and *Aspergillus oryzae* | |
| Toyocerin ® | Rubinum | *Bacillus cereus* | |
| TOYOCERIN ® | Rubinum | *Bacillus cereus* var. *toyoi* NCIMB 40112/CNCM I-1012 | |

In one embodiment suitably the DFM may be Enviva Pro®.

Enviva Pro® is commercially available from Danisco A/S and is a combination of *Bacillus* strain 2084 Accession No. NRRI B-50013, *Bacillus* strain LSSAO1 Accession No. NRRL B-50104 and *Bacillus* strain 15A-P4 ATCC Accession No. PTA-6507 (as taught in U.S. Pat. No. 7,754,469 B—incorporated herein by reference).

In one embodiment the DFM may be *Bacillus licheniformis* BL21 (NRRL B-50134).

AgTech Products, Inc. of W227 N752 Westmound Drive, Waukesha, Wis. 53186, USA deposited under the Budapest Treaty the following biological deposit with the Agricultural Research Service Culture Collection (NRRL) with the date of the original deposit and accession number detailed below:

| | | |
|---|---|---|
| *Bacillus licheniformis* BL21 | NRRL B-50134 | 15 Apr. 2008 |
| *Enterococcus faecium* EF141 (EN-1) | NRRL B-30981 | 30 Oct. 2006 |
| *Enterococcus faecium* 2-1d | NRRL B-50519 | 3 Jun. 2011 |
| *Lactobacillus acidophilus* A2020 | NRRL B-30977 | 24 Oct. 2006 |
| *Lactobacillus acidophilus* A4000h | NRRL B-30978 | 24 Oct. 2006 |
| *Lactobacillus acidophilus* PIBc6 | NRRL B-50103 | 18 Jan. 2008 |
| *Lactobacillus brevis* LBR 1000 | NRRL B-30982 | 30 Oct. 2006 |
| *Lactobacillus casei* LC222 | NRRL B-30983 | 30 Oct. 2006 |
| *Lactobacillus johnsonii* PLCB6 | NRRL B-50518 | 6 Jun. 2011 |
| *Lactobacillus salivarius* o246i33w | NRRL B-50102 | 18 Jan. 2008 |

| | | |
|---|---|---|
| Pediococcus acidilactici PIJe3 | NRRL B-50101 | 18 Jan. 2008 |
| Pediococcus acidilactici o246e42 | NRRL B-50171 | 29 Aug. 2008 |

AgTech Products, Inc has authorised DuPont Nutrition Biosciences ApS of Langebrogade 1, PO Box 17, DK-1001, Copenhagen K, Denmark to refer to all of these deposited biological material in this patent application and has given unreserved and irrevocable consent to the deposited material being made available to the public.

AgTech Products, Inc. of W227 N752 Westmound Drive, Waukesha, Wis. 53186, USA also deposited under the Budapest Treaty the following biological deposits with the American Type Culture Collection (ATCC), Manassas, Va. 20110-2209, USA (PTA references) or with the Agricultural Research Service Culture Collection (NRRL references) with the dates of the original deposits and accession numbers detailed below—these strains are referred to in the patents listed in the table and as such are publicly available strains:

| | | | |
|---|---|---|---|
| Lactobacillus brevis AJ25 | PTA-6099 | 22 Jun. 2006 | U.S. Pat. No. 7,384,628 B |
| Lactobacillus brevis HE17 | PTA-6100 | 22 Jun. 2006 | U.S. Pat. No. 7,384,628 B |
| Lactobacillus brevis 1E-1 | PTA-6509 | 12 Jan. 2005 | U.S. Pat. No. 7,354,757 B |
| Lactobacillus lactis CI15 | PTA-6101 | 22 Jun. 2004 | U.S. Pat. No. 7,384,628 B |
| Lactobacillus lactis DJ6 | PTA-6102 | 22 Jun. 2004 | U.S. Pat. No. 7,384,628 B |
| Lactococcus lactis ID7 | PTA 6103 | 22 Jun. 2004 | U.S. Pat. No. 7,384,628 B |
| Lactococcus lactis JD19 | PTA 6104 | 22 Jun. 2004 | U.S. Pat. No. 7,384,628 B |
| Propionibacterium acidipropionici P261 | NRRL B-50131 | 2 Apr. 2008 | U.S. Pat. No. 7,470,531 B & U.S. Pat. No. 6,951,643 B |
| Propionibacterium acidipropionici P179 | NRRL B-50133 | 2 Apr. 2008 | U.S. Pat. No. 7,470,531 B & U.S. Pat. No. 6,951,643 B |
| Propionibacterium acidipropionici P169 | PTA 5271 | 18 Jun. 2003 | U.S. Pat. No. 7,470,531 B & U.S. Pat. No. 6,951,643 B |
| Propionibacterium acidipropionici P170 | PTA 5272 | 18 Jun. 2003 | U.S. Pat. No. 7,470,531 B & U.S. Pat. No. 6,951,643 B |
| Propionibacterium jensenii P63 | NRRL B-30979 | 24 Oct. 2006 | U.S. Pat. No. 5,945,333 B |
| Propionibacterium jensenii P195 | NRRL B-50132 | 2 Apr. 2008 | U.S. Pat. No. 7,470,531 B & U.S. Pat. No. 6,951,643B |

In one embodiment the DFM for use in the present invention is selected from the group consisting of: *Bacillus subtilis* BS18 (NRRL B-50633), *Bacillus subtilis* BS278 (NRRL 50634), *Bacillus subtilis* 4-7 d (NRRL B-50505), *Bacillus subtilis* 3-5 h (NRRL B-50507), *Bacillus subtilis* AGTP BS3BP5 (NRRL B-50510), *Bacillus subtilis* BS918 (NRRL B-50508), *Bacillus subtilis* AGTP BS1013 (NRRL-50509), *B. subtilis* AGTP 944 (NRRL B-50548), *Bacillus subtilis* AGTP BS442 (NRRL B-50542), *B. subtilis* AGTP BS1069 (NRRL B-50544), *B. subtilis* AGTP BS521 (NRRL B-50545), *B. subtilis* BS2084 (NRRL B-50013), *B. subtilis* LSSA01 (NRRL B-50104), *B. subtilis* B27 (NRRL B-50105), *B. subtilis* 3A-P4 (PTA-6506), *Bacillus subtilis* 15A-P4 (PTA-6507), *B. subtilis* 22C-P1 (PTA-6508), *B. subtilis* BL21 (NRRL B-50134), *Bacillus licheniformis* BL21 (NRRL B-50134), *Bacillus licheniformis* 3-12a (NRRL B-50504), *Bacillus licheniformis* 4-2a (NRRL B-50506), *Bacillus licheniformis* 842 (NRRL B-50516), *Propionibacterium acidipropionici* P261 (NRRL B-50131), *Propionibacterium acidipropionici* P179 (NRRL B-50133), *Propionibacterium acidipropionici* P169 (PTA 5271), *Propionibacterium acidipropionici* P170 (PTA 5272), *Propionibacterium jensenii* P63 (NRRL B-30979), *Propionibacterium jensenii* P195 (NRRL B-50132), *Lactococcus lactis* ID7 (PTA 6103), *Lactococcus lactis* JD19 (PTA 6104), *Lactobacillus acidophilus* A2020 (NRRL B-30977), *Lactobacillus acidophilus* A4000 h (NRRL B-30978), *Lactobacillus acidophilus* PIBc6 (NRRL B-50103), *Lactobacillus brevis* LBR 1000 (NRRL B-30982), *Lactobacillus casei* LC222 (NRRL B-30983), *Lactobacillus johnsonii* PLCB6 (NRRL B-50518), *Lactobacillus salivarius* o246i33w (NRRL B-50102), *Lactobacillus brevis* AJ25 (PTA-6099), *Lactobacillus brevis* HE17 (PTA-6100), *Lactobacillus brevis* 1E-1 (PTA-6509), *Lactobacillus lactis* CI15 (PTA-6101), *Lactobacillus lactis* DJ6 (PTA-6102), *Lactobacillus rhamnosus* (CNCM 1-3698), *Lactobacillus* farciminis (CNCM 1-3699), *Enterococcus faecium* EF141 (EN-1) (NRRL B-30981), *Enterococcus faecium* 2-1 d (NRRL B-50519), *Pediococcus acidilactici* PlJe3 (NRRL B-50101), *Pediococcus acidilactici* o246e42 (NRRL B-50171) and combinations thereof. Suitably, the DFM may comprise a yeast from the genera: *Saccharomyces* spp.

Preferably the DFM to be used in accordance with the present invention is a microorganism which is generally recognised as safe and, which is preferably GRAS approved.

A skilled person will readily be aware of specific species and or strains of microorganisms from within the genera described herein which are used in the food and/or agricultural industries and which are generally considered suitable for animal consumption.

Preferably, the DFM used in accordance with the present invention is one which is suitable for animal consumption.

Advantageously, where the product is a feed or feed additive composition, the viable DFM should remain effective through the normal "sell-by" or "expiration" date of the product during which the feed or feed additive composition is offered for sale by the retailer. The desired lengths of time and normal shelf life will vary from feedstuff to feedstuff and those of ordinary skill in the art will recognise that shelf-life times will vary upon the type of feedstuff, the size of the feedstuff, storage temperatures, processing conditions, packaging material and packaging equipment.

In some embodiments it is important that the DFM is tolerant to heat, i.e. is thermotolerant. This is particularly the case where the feed is pelleted. Therefore in one embodiment the DFM may be a thermotolerant microorganism, such as a thermotolerant bacteria, including for example *Bacillus* spp.

In some embodiments it may be preferable that the DFM is a spore producing bacteria, such as Bacilli, e.g. *Bacillus* spp. Bacilli are able to from stable endospores when conditions for growth are unfavorable and are very resistant to heat, pH, moisture and disinfectants.

In one embodiment suitably the DFM may decrease or prevent intestinal establishment of pathogenic microorganism (such as *Clostridium perfringens* and/or *E. coli* and/or *Salmonella* spp and/or *Campylobacter* spp., preferably *Clostridium perfringens* and/or *E. coli*).

The DFM according to the present invention may be any suitable DFM. In one embodiment the following assay "DFM ASSAY" may be used to determine the suitability of a microorganism to be a DFM. For the avoidance of doubt in one embodiment a DFM selected as an inhibitory strain (or an antipathogen DFM) in accordance with the "DFM ASSAY" taught herein is a suitable DFM for use in accordance with the present invention, i.e. in the feed additive composition according to the present invention.

DFM Assay:

Tubes were seeded each with a representative pathogen from a representative cluster. Supernatant from a potential DFM grown aerobically or anaerobically was added to the seeded tubes and incubated.

After incubation, the optical density (OD) of the control and supernatant treated tubes was measured for each pathogen.

Colonies of (potential DFM) strains that produced a lowered OD compared with the control were classified as an inhibitory strain (or an antipathogen DFM).

The DFM assay as used herein is explained in more detail in US2009/0280090—incorporated herein by reference.

Preferably the representative pathogen used in assay is one (or more) of the following: *Clostridium*, such as *Clostridium perfringens* and/or *Clostridium difficile*, and/or *E. coli* and/or *Salmonella* spp and/or *Campylobacter* spp. In one preferred embodiment the assay is conducted with one or more of *Clostridium perfringens* and/or *Clostridium difficile* and/or *E. coli*, preferably *Clostridium perfringens* and/or *Clostridium difficile*, more preferably *Clostridium perfringens*.

In one embodiment the DFM of the present invention is preferably an antipathogen.

The term "antipathogen" as used herein means that the DFM counters an effect (e.g. a negative effect) of a pathogen.

In one embodiment to determine if a DFM is an antipathogen in accordance with the present invention the above mentioned DFM assay may be used. A DFM is considered to be an antipathogen or an antipathogen DFM if it is classed as an inhibitory strain in the above mentioned DFM assay, particularly when the pathogen is *Clostridium perfringens*.

In one embodiment the antipathogen DFM may be one or more of the following bacteria:

*Bacillus subtilis* strain 2084 Accession No. NRRL B-50013,
*Bacillus subtilis* strain LSSAO1 Accession No. NRRL B-50104,
*Bacillus subtilis* strain 15A-P4 ATCC Accession No. PTA-6507,
*Bacillus subtilis* strain 3A-P4 ATCC Accession No. PTA-6506, and
*Bacillus subtilis* strain BS27 ATCC Accession No. NRRL B-50105.

For the avoidance of doubt these strains are available and are referred to in U.S. Pat. No. 7,754,459 B. In one embodiment the DFM used in accordance with the present invention is not *Lactobacillus* gasseri BNR 17 Strain Acc No. KCTC 10902BP as taught in WO2008/016214.

Preferably the DFM is not an inactivated microorganism.

In one embodiment the DFM as used here is a composition comprising one or more DFM microorganisms as described herein. The composition may additionally comprise the enzyme of the present invention.

The composition can be fed to an animal as a direct-fed microbial (DFM).

One or more carrier(s) or other ingredients can be added to the DFM.

The DFM may be presented in various physical forms, for example, as a top dress, as a water soluble concentrate for use as a liquid drench or to be added to a milk replacer, gelatin capsule, or gels.

In one embodiment of the top dress form, freeze-dried fermentation product is added to a carrier, such as whey, maltodextrin, sucrose, dextrose, limestone (calcium carbonate), rice hulls, yeast culture, dried starch, and/or sodium silico aluminate.

In one embodiment of the water soluble concentrate for a liquid drench or milk replacer supplement, freeze-dried fermentation product is added to a water soluble carrier, such as whey, maltodextrin, sucrose, dextrose, dried starch, sodium silico aluminate, and a liquid is added to form the drench or the supplement is added to milk or a milk replacer.

In one embodiment of the gelatin capsule form, freeze-dried fermentation product is added to a carrier, such as whey, maltodextrin, sugar, limestone (calcium carbonate), rice hulls, yeast culture dried starch, and/or sodium silico aluminate.

In one embodiment, the bacteria and carrier are enclosed in a degradable gelatin capsule. In one embodiment of the gels form, freeze-dried fermentation product is added to a carrier, such as vegetable oil, sucrose, silicon dioxide, polysorbate 80, propylene glycol, butylated hydroxyanisole, citric acid, ethoxyquin, and/or artificial coloring to form the gel.

The DFM(s) may optionally be admixed with a dry formulation of additives including but not limited to growth substrates, enzymes, sugars, carbohydrates, extracts and growth promoting micro-ingredients. The sugars could include the following: lactose; maltose; dextrose; maltodextrin; glucose; fructose; mannose; tagatose; sorbose; raffinose; and galactose. The sugars range from 50-95%, either individually or in combination. The extracts could include yeast or dried yeast fermentation solubles ranging from 5-50%. The growth substrates could include: trypticase, ranging from 5-25%; sodium lactate, ranging from 5-30%; and, Tween 80, ranging from 1-5%. The carbohydrates could include mannitol, sorbitol, adonitol and arabitol. The carbohydrates range from 5-50% individually or in combination. The micro-ingredients could include the following: calcium carbonate, ranging from 0.5-5.0%; calcium chloride, ranging from 0.5-5.0%; dipotassium phosphate, ranging from 0.5-5.0%; calcium phosphate, ranging from 0.5-5.0%; manganese proteinate, ranging from 0.25-1.00%; and, manganese, ranging from 0.25-1.0%.

To prepare DFMs described herein, the culture(s) and carrier(s) (where used) can be added to a ribbon or paddle mixer and mixed for about 15 minutes, although the timing can be increased or decreased. The components are blended such that a uniform mixture of the cultures and carriers result. The final product is preferably a dry, flowable powder. The DFM(s) or composition comprising same can then be added to animal feed or a feed premix, added to an animal's water, or administered in other ways known in the art (preferably simultaneously with the enzymes of the present invention). A feed for an animal can be supplemented with one or more DFM(s) described herein or with a composition described herein.

By "a mixture of at least two strains," is meant a mixture of two, three, four, five, six or even more strains. In some embodiments of a mixture of strains, the proportions can vary from 1% to 99%. Other embodiments of a mixture of strains are from 25% to 75%. Additional embodiments of a mixture of strains are approximately 50% for each strain. When a mixture comprises more than two strains, the strains can be present in substantially equal proportions or in different proportions in the mixture.

In one embodiment the DFM may be a viable or inviable microorganism which is used in isolated or semi-isolated form. The DFM may be used in combination with or without the growth medium in which it was cultured.

In one embodiment, the DFM is capable of producing colony forming units when grown on an appropriate media. The appropriate media may comprise (or consist of) a feed or a feed constituent.

In one embodiment, the DFM is incapable of producing colony forming units when grown on an appropriate media. The appropriate media may comprise (or consist of) a feed or a feed constituent.

Irrespective of whether the DFM is capable or incapable of producing colony forming units when grown on an appropriate media—the cells may be still metabolically active (e.g. even if they are unable to divide).

In one embodiment the DFM may be administered as inviable cells.

In one embodiment the DFM may be administered as a viable microorganism.

The DFM may be dosed appropriately.

Suitably dosages of DFM in the feed may be between about $1 \times 10^3$ CFU/g feed to about $1 \times 10^9$ CFU/g feed, suitably between about $1 \times 10^4$ CFU/g feed to about $1 \times 10^8$ CFU/g feed, suitably between about $7.5 \times 10^4$ CFU/g feed to about $1 \times 10^7$ CFU/g feed.

In one embodiment the DFM is dosed in the feedstuff at more than about $1 \times 10^3$ CFU/g feed, suitably more than about $1 \times 10^4$ CFU/g feed, suitably more than about $7.5 \times 10^4$ CFU/g feed. Suitably dosages of DFM in the feed additive composition may be between about $2 \times 10^2$ CFU/g composition to about $1 \times 10^{10}$ CFU/g composition, suitably between about $1 \times 10^3$ CFU/g composition to about $1 \times 10^{10}$ CFU/g composition, suitably between about $1 \times 10^4$ CFU/g composition to about $1 \times 10^9$ CFU/g composition suitably between about $3.75 \times 10^4$ CFU/g composition to about $3 \times 10^8$ CFU/g composition.

In one embodiment the DFM is dosed in the feed additive composition at more than about $1 \times 10^5$ CFU/g composition, suitably more than about $1 \times 10^6$ CFU/g composition, suitably more than about $3.75 \times 10^7$ CFU/g composition.

As used herein the term "CFU" means colony forming units and is a measure of viable cells in which a colony represents an aggregate of cells derived from a single progenitor cell.

Phytase

As used herein, the term "phytase" refers to an enzyme (i.e. a polypeptide having phytase activity) that catalyzes the hydrolysis of esters of phosphoric acid, including phytate and phytic acid, and releases inorganic phosphate.

The phytase for use in the present invention may be classified a 6-phytase (classified as E.C. 3.1.3.26) or a 3-phytase (classified as E.C. 3.1.3.8).

In one embodiment the phytase may be a 6-phytase (E.C. 3.1.3.26).

In one preferred embodiment the phytase for use in the present invention may be one or more of the phytases in one or more of the commercial products below:

| Commercial product ® | Company | Phytase type | Phytase source |
|---|---|---|---|
| AxtraPHY | Danisco Animal Nutrition | 6-phytase | *Buttiauxella* sp. |
| Phyzyme XP | Danisco | 6-phytase | *E. coli* gene expressed in *Schizosaccahomyces pombe* |
| Ronozyme Hi-Phos (M/L) | DSM/Novozymes | 6-phytase | *Citrobacter braakii* gene expressed in *Aspergillus oryzae* |
| Finase | ABVista | 3-phytase | *Trichoderma reesei* |
| Finase EC | ABVista | 6-phytase | *E. coli* gene expressed in *Trichoderma reesei* |
| Natuphos | BASF | 3-phytase | *Aspergillus Niger* |
| Natuzyme | Bioproton | phytase (type not specified) | *Trichoderma longibrachiatum/ Trichoderma reesei* |
| OPTIPHOS ® | Huvepharma AD | 6-phytase | *E. coli* gene expressed in *Pichia pastoris* |
| Phytase sp1002 | DSM | 3-phytase | A consensus gene expressed in *Hansenula polymorpha* |
| Quantum Blue | ABVista | 6-phytase | *E. coli* gene expressed in *Trichoderma* |
| Quantum 2500D, 5000L | ABVista | 6-phytase | *E. coli* gene expressed in *Pichia pastoris* or *Trichoderma* |
| Ronozyme NP | DSM/Novozymes | 6-phytase | *Peniphora lycii* gene expressed in *Aspergillus oryzae* |
| Ronozyme P | DSM/Novozymes | 6-phytase | *Peniphora lycii* gene expressed in *Aspergillus oryzae* |
| Rovabio PHY | Adisseo | 3-phytase | *Penicillium funiculosum* |

The term consensus gene as used herein means that the DNA vector used to transform the organism contains a synthetic phytase gene based on a consensus sequence, a URA gene from the non-pathogenic yeast *Saccharomyces cerevisiae* and the origin of replication of the *Escherichia coli* plasmid pBR322.

In one embodiment the phytase is a *Citrobacter* phytase derived from e.g. *Citrobacter freundii*, preferably *C. freundii* NCIMB 41247 and variants thereof e.g. as disclosed in WO2006/038062 (incorporated herein by reference) and WO2006/038128 (incorporated herein by reference), *Citrobacter braakii* YH-15 as disclosed in WO 2004/085638, *Citrobacter braakii* ATCC 51113 as disclosed in WO2006/037328 (incorporated herein by reference), as well as variants thereof e.g. as disclosed in WO2007/112739 (incorporated herein by reference) and WO2011/117396 (incorporated herein by reference), *Citrobacter amalonaticus*, preferably *Citrobacter amalonaticus* ATCC 25405 or *Citrobacter amalonaticus* ATCC 25407 as disclosed in WO2006037327 (incorporated herein by reference), *Citrobacter gillenii*, preferably *Citrobacter gillenii* DSM 13694 as disclosed in WO2006037327 (incorporated herein by reference), or *Citrobacter intermedius, Citrobacter koseri, Citrobacter murliniae, Citrobacter rodentium, Citrobacter sedlakii, Citrobacter werkmanii, Citrobacter youngae, Citrobacter* species polypeptides or variants thereof.

In one embodiment the phytase may be a phytase from *Citrobacter*, e.g. from *Citrobacter freundii*, such as the phytase enzyme(s) taught in WO2006/038128, which reference is incorporated herein by reference.

In preferred embodiments, the phytase is preferably *E. coli* phytase marketed under the name Phyzyme XP™ by Danisco A/S.

Alternatively the phytase may be a *Buttiauxella* phytase, e.g. a *Buttiauxella agrestis* phytase, for example, the phytase enzymes taught in WO 2006/043178, WO 2008/097619, WO2009/129489, WO2006/038128, WO2008/092901, PCT/US2009/41011 or PCT/162010/051804, all of which are incorporated herein by reference.

In one aspect, the enzyme used is BP17 or a polypeptide shown in SEQ ID No. 1 or SEQ ID No. 2 or a variant thereof, such as a sequence having at least 70% identity thereto, preferably having at least 75% identity thereto, preferably having at least 80% identity thereto, preferably having at least 85% identity thereto, preferably having at least 90% identity thereto, preferably having at least 95% identity thereto, preferably having at least 96% identity thereto, preferably having at least 97% identity thereto, preferably having at least 98% identity thereto, preferably having at least 99% identity thereto. BP17 is an enzyme variant of a *Buttiauxella* sp. Phytase and is described in e.g. WO2008/097619, which reference is incorporated herein by reference.

In one embodiment, the enzyme used is BP17 and described in e.g. WO2008/097619. BP17 is an enzyme variant of a *Buttiauxella* sp. phytase.

The sequence for BP17 (excluding signal peptide) is shown as SEQ ID No. 1. The sequence for BP17 including the signal peptide (underlines) is shown as SEQ ID No. 2.

SEQ ID NO: 1:
NDTPASGYQVEKVVILSRHGVRAPTKMTQTMRDVTPNTWPEWPVKLGYIT

PRGEHLISLMGGFYRQKFQQQGILSQGSCPTPNSIYVWTDVAQRTLKTGE

AFLAGLAPQCGLTIHHQQNLEKADPLFHPVKAGICSMDKTQVQQAVEKEA

QTPIDNLNQHYIPSLALMNTTLNFSKSPWCQKHSADKSCDLGLSMPSKLS

IKDNGNEVSLDGAIGLSSTLAEIFLLEYAQGMPQAAWGNIHSEQEWALLL

KLHNVYFDLMERTPYIARHKGTPLLQAISNALNPNATESKLPDISPDNKI

LFIAGHDTNIANIAGMLNMRWTLPGQPDNTPPGGALVFERLADKSGKQYV

SVSMVYQTLEQLRSQTPLSLNQPAGSVQLKIPGCNDQTAEGYCPLSTFTR

VVSQSVEPGCQLQ

SEQ ID NO: 2:
*MTISAFNRKKLTLHPGLFVALSAIFSLGSTAYA*NDTPASGYQVEKVVILS

RHGVRAPTKMTQTMRDVTPNTWPEWPVKLGYITPRGEHLISLMGGFYRQK

FQQQGILSQGSCPTPNSIYVWTDVAQRTLKTGEAFLAGLAPQCGLTIHHQ

QNLEKADPLFHPVKAGICSMDKTQVQQAVEKEAQTPIDNLNQHYIPSLAL

MNTTLNFSKSPWCQKHSADKSCDLGLSMPSKLSIKDNGNEVSLDGAIGLS

STLAEIFLLEYAQGMPQAAWGNIHSEQEWALLLKLHNVYFDLMERTPYIA

RHKGTPLLQAISNALNPNATESKLPDISPDNKILFIAGHDTNIANIAGML

NMRWTLPGQPDNTPPGGALVFERLADKSGKQYVSVSMVYQTLEQLRSQTP

LSLNQPAGSVQLKIPGCNDQTAEGYCPLSTFTRVVSQSVEPGCQLQ

In one embodiment the phytase is the AxtraPHY™ phytase.

The AxtraPHY™ phytase is also known as the BP17 phytase herein.

In one embodiment the phytase may be a phytase from Hafnia, e.g. from Hafnia *alvei*, such as the phytase enzyme (s) taught in US2008263688, which reference is incorporated herein by reference.

In one embodiment the phytase may be a phytase from *Aspergillus*, e.g. from *Apergillus orzyae*.

In one embodiment the phytase may be a phytase from *Penicillium*, e.g. from *Penicillium funiculosum*.

The term "phytase" may be one phytase or a combination of phytases unless the context clearly dictates otherwise.

Preferably, the phytase is present in the feedstuff in range of about 1500 FTU/kg to about 20000 FTU/kg feed, suitably about 1500 FTU/kg to about 10000 FTU/kg feed, suitably about 1500 FTU/kg feed to about 5000 FTU/kg feed, suitably about 1500 FTU/kg feed to about 3000 FTU/kg feed, more preferably about 2000 FTU/kg feed to about 20000 FTU/kg feed, suitably about 2000 FTU/kg feed to about 10000 FTU/kg feed, suitably about 2000 FTU/kg feed to about 5000 FTU/kg feed, suitably about 2000 FTU/kg feed to about 3500 FTU/kg feed.

In one embodiment the phytase is present in the feedstuff at more than about 1500 FTU/kg feed, suitably more than about 2000 FTU/kg feed, suitably more than about 3000 FTU/kg feed. In one embodiment the phytase is present in the feedstuff at less than about 15000 FTU/kg feed, suitably less than about 12000 FTU/kg feed.

In one embodiment, the phytase is present in the feedstuff in range of about 1500 FTU/kg to about 5000 FTU/kg feed.

In one embodiment, the phytase is present in the feedstuff in range of about 2000 FTU/kg to about 5000 FTU/kg feed.

In a preferred embodiment, the phytase is present in the feedstuff in range of about 1500 FTU/kg to about 3000 FTU/kg feed.

In a much preferred embodiment, the phytase is present in the feedstuff in range of about 2000 FTU/kg to about 3000 FTU/kg feed.

In one embodiment, the phytase may be present in the feed additive composition:
 a. at about 30,000 FTU/g composition or more when the composition is dosed (e.g. the manufacturer's recommended dose) in a feed is equal to or greater than 50 g/metric ton (MT) of feed,
 b. at about 20,000 FTU/g composition or more when the composition is dosed (e.g. the manufacturer's recommended dose) in a feed is equal to or greater than 75 g/metric ton (MT) of feed,
 c. at about 15,000 FTU/g composition or more when the composition is dosed (e.g. the manufacturer's recommended dose) in a feed is equal to or greater than 100 g/metric ton (MT) of feed,
 d. at about 15,000 FTU/g composition or more when the composition is dosed (e.g. the manufacturer's recommended dose) in a feed is equal to or greater than 100 g/metric ton (MT) of feed,
 e. at about 10,000 FTU/g composition or more when the composition is dosed (e.g. the manufacturer's recommended dose) in a feed is equal to or greater than 150 g/metric ton (MT) of feed,
 f. at about 7,500 FTU/g composition or more when the composition is dosed (e.g. the manufacturer's recommended dose) in a feed is equal to or greater than 200 g/metric ton (MT) of feed,
 g. at about 5,000 FTU/g composition or more when the composition is dosed (e.g. the manufacturer's recommended dose) in a feed is equal to or greater than 300 g/metric ton (MT) of feed.

Suitably when the phytase is present in the feed additive composition in the dosages given above the direct fed microbial is present in the feed additive composition in a range from $2.5 \times 10^3$ CFU DFM: 1 FTU enzyme to $6.7 \times 10^6$ CFU:1 FTU enzyme, suitably in a range from $3.8 \times 10^3$ CFU DFM: 1 FTU enzyme to $2.0 \times 10^5$ CFU:1 FTU enzyme.

It will be understood that as used herein 1 FTU (phytase unit) is defined as the amount of enzyme required to release 1 µmol of inorganic orthophosphate from a substrate in one minute under the reaction conditions defined in the ISO 2009 phytase assay—A standard assay for determining phytase activity and 1 FTU can be found at *International Standard ISO/DIS* 30024: 1-17, 2009.

In one embodiment suitably the enzyme is classified using the E.C. classification above, and the E.C. classification designates an enzyme having that activity when tested in the assay taught herein for determining 1 FTU.

Advantages

The interaction of DFMs with enzymes is complicated and without wishing to be bound by theory, it is very surprising that we can see an improvement in the subject's resistance to necrotic enteritis. Prior to the present invention the specific combination of DFMs and high phytase (e.g. as taught herein) had not been taught for this specific purpose.

In addition or alternatively in terms of animal performance, e.g. feed conversion ratio, there is a synergistic effect in the combination of a DFM (e.g. antipathogen DFM) with phytase, when the phytase is dosed above 1500 FTU/kg feed. When phytase is supplemented alone, there is an increase in performance (i.e. reduction in FCR) at 500 and 1500 FTU/kg feed and a reduction in performance (i.e. an increase in FCR) when the phytase dose exceeds about 1500 FTU/kg feed. This is particularly true in the conditions of a necrotic enteritis challenge. However, when the DFM is added in combination with phytase above 1500 FTU/kg feed, there is a consistent numerical increase in performance (i.e. reduction in the FCR) compared to the phytase only treatments. Between the level of 3000 FTU/kg feed and 10,000 FTU/kg feed there is a large numerical reduction which results in the lowest FCR of all of the treatment groups. Surprisingly the combination of DFM (particularly antipathogen DFM) with phytase at more than 1500 FTU/kg feed results in a synergistic combination.

An advantage of the present invention is that the combination of DFMs (e.g. antipathogen) DFMs with high dose phytase significantly improves the efficacy of the phytase to improve animal performance and/or phosphorus retention in a subject.

A further advantage of the present invention is the combination of DFMs (e.g. antipathogen) DFMs with high dose phytase improves phosphorus (e.g. dietary phosphorus) absorption and retention in a subject. This combinational effect was completely unexpected.

One advantage of the present invention is that the feed additive composition according to the present invention can avoid the negative effects of necrotic enteritis or can be used for improving the subject's resistance to necrotic enteritis.

Without wishing to be bound by theory, phytase catalyzes the sequential hydrolysis of phytate, a principal storage form of phosphorus in cereals and legumes, to less phosphorylated myo-inositol derivatives with concomitant release of inorganic phosphate. Hydrolysis of phytate causes a reduction of endogenous losses of amino acids to the intestinal lumen. A reduction of endogenous amino acid losses in the intestine reduces the availability of nitrogen for bacterial growth, which helps the activity of DFMs on inhibition of *C. perfringens* and other pathogenic bacteria.

Without wishing to be bound by theory adding phytase enzymes and hydrolysing phytate, can result in an increase in the pH of the small intestine (duodenum, jejenum and/or ileum). Phytase may also actually increase the amount of bacteria of species *E. coli* and *C. perfringens*. This may be associated with a higher pH. The present inventors have found that the addition of a DFM (particularly an antipathogen DFM) with high doses of phytases may offset the increase in pathogenic bacteria.

High doses of phytase increase the hydrolysis of phytic acid in the gut of animals, which can have advantages for increased digestibility of phosphorus, calcium, energy, protein and other nutrients and possibly animal performance. Surprisingly, however, the inventors have found that high doses of phytase cannot achieve the potential improvements on nutrient digestibility and animal performance when clinical or subclinical intestinal disease challenge is present, e.g. necrotic enteritis in broilers, which is a common occurrence in commercial animal production. By combining high doses of phytases with an antipathogenic DFM the inventors have surprisingly found that animal performance is further enhanced even at very high levels of phytase (e.g. 10,000 FTU/kg feed).

In combination high dosages of phytase and DFMs surprisingly provides a significant improvement on the pathogen reduction and/or resistance to necrotic enteritis and/or feed conversion ratio, and/or body weight gain and/or performance of a subject and/or reducing nutrient excretion in manure compared with DFMs in combination with standard (low) phytase dosages and/or DFMs alone and/or enzyme (even high dosage phytase) alone.

Formulation of the DFM with the Enzymes

The DFM and the enzyme(s) may be formulated in any suitable way to ensure that the formulation comprises viable DFMs and active enzyme(s).

In one embodiment the DFM and enzyme(s) may be formulated as a liquid, a dry powder or a granule.

The dry powder or granules may be prepared by means known to those skilled in the art, such as, in top-spray fluid bed coater, in a buttom spray Wurster or by drum granulation (e.g. High sheer granulation), extrusion, pan coating or in a microingredients mixer.

For some embodiments the DFM and/or the enzyme(s) may be coated, for example encapsulated. Suitably the DFM and enzyme may be formulated within the same coating or encapsulated within the same capsule. Alternatively the enzyme(s) may be formulated within one coating or encapsulated within one capsule and the DFM could be formulated in a coating separate to the enzyme(s). In some embodiments, such as where the DFM is capable of producing endospores, the DFM may be provided without any coating. In such circumstances, the DFM endospores may be simply admixed with the enzyme(s). In the latter case, the enzyme(s) may be coated, e.g. encapsulated.

In one embodiment the coating protects the enzyme(s) from heat and may be considered a thermoprotectant.

In one embodiment the feed additive composition is formulated to a dry powder or granules as described in WO2007/044968 (referred to as TPT granules) or WO1997/016076 or WO1992/012645 (each of which is incorporated herein by reference).

In one embodiment the feed additive composition may be formulated to a granule for feed compositions comprising: a core; an active agent; and at least one coating, the active agent of the granule retaining at least 50% activity, at least 60% activity, at least 70% activity, at least 80% activity after conditions selected from one or more of a) a feed pelleting process, b) a steam-heated feed pretreatment process, c) storage, d) storage as an ingredient in an unpelleted mixture, and e) storage as an ingredient in a feed base mix or a feed premix comprising at least one compound selected from trace minerals, organic acids, reducing sugars, vitamins, choline chloride, and compounds which result in an acidic or a basic feed base mix or feed premix.

With regard to the granule at least one coating may comprise a moisture hydrating material that constitutes at least 55% w/w of the granule; and/or at least one coating may comprise two coatings. The two coatings may be a moisture hydrating coating and a moisture barrier coating. In some embodiments, the moisture hydrating coating may be between 25% and 60% w/w of the granule and the moisture barrier coating may be between 2% and 15% w/w of the granule. The moisture hydrating coating may be selected from inorganic salts, sucrose, starch, and maltodextrin and the moisture barrier coating may be selected from polymers, gums, whey and starch.

The granule may be produced using a feed pelleting process and the feed pretreatment process may be conducted between 70° C. and 95° C. for up to several minutes, such as between 85° C. and 95° C.

In one embodiment the feed additive composition may be formulated to a granule for animal feed comprising: a core; an active agent, the active agent of the granule retaining at least 80% activity after storage and after a steam-heated pelleting process where the granule is an ingredient; a moisture barrier coating; and a moisture hydrating coating that is at least 25% w/w of the granule, the granule having a water activity of less than 0.5 prior to the steam-heated pelleting process.

The granule may have a moisture barrier coating selected from polymers and gums and the moisture hydrating material may be an inorganic salt. The moisture hydrating coating may be between 25% and 45% w/w of the granule and the moisture barrier coating may be between 2% and 10% w/w of the granule.

The granule may be produced using a steam-heated pelleting process which may be conducted between 85° C. and 95° C. for up to several minutes.

In some embodiments the DFM (e.g. DFM endospores for example) may be diluted using a diluent, such as starch powder, lime stone or the like.

In one embodiment, the composition is in a liquid formulation suitable for consumption preferably such liquid consumption contains one or more of the following: a buffer, salt, sorbitol and/or glycerol.

In another embodiment the feed additive composition may be formulated by applying, e.g. spraying, the enzyme(s) onto a carrier substrate, such as ground wheat for example.

In one embodiment the feed additive composition according to the present invention may be formulated as a premix. By way of example only the premix may comprise one or more feed components, such as one or more minerals and/or one or more vitamins.

In one embodiment the DFM and/or enzyme(s) for use in the present invention are formulated with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, etabisulfite, formate and mixtures thereof.

Packaging

In one embodiment the feed additive composition and/or premix and/or feed or feedstuff according to the present invention is packaged.

In one preferred embodiment the feed additive composition and/or premix and/or feed or feedstuff is packaged in a bag, such as a paper bag.

In an alternative embodiment the feed additive composition and/or premix and/or feed or feedstuff may be sealed in a container. Any suitable container may be used.

Feed or Feedstuff

The feed additive composition of the present invention may be used as—or in the preparation of—a feed.

The term "feed" is used synonymously herein with "feedstuff".

The feed may be in the form of a solution or as a solid—depending on the use and/or the mode of application and/or the mode of administration.

When used as—or in the preparation of—a feed—such as functional feed—the composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

In a preferred embodiment the feed additive composition of the present invention is admixed with a feed component to form a feedstuff.

The term "feed component" as used herein means all or part of the feedstuff. Part of the feedstuff may mean one constituent of the feedstuff or more than one constituent of the feedstuff, e.g. 2 or 3 or 4. In one embodiment the term "feed component" encompasses a premix or premix constituents.

Preferably the feed may be a fodder, or a premix thereof, a compound feed, or a premix thereof. In one embodiment the feed additive composition according to the present invention may be admixed with a compound feed, a compound feed component or to a premix of a compound feed or to a fodder, a fodder component, or a premix of a fodder.

The term fodder as used herein means any food which is provided to an animal (rather than the animal having to forage for it themselves). Fodder encompasses plants that have been cut.

The term fodder includes silage, compressed and pelleted feeds, oils and mixed rations, and also sprouted grains and legumes.

Fodder may be obtained from one or more of the plants selected from: barley rapeseed (canola), corn (maize), millet, oats, sorghum, soybeans, wheat, and legumes.

The term "compound feed" means a commercial feed in the form of a meal, a pellet, nuts, cake or a crumble. Compound feeds may be blended from various raw materials and additives.

These blends are formulated according to the specific requirements of the target animal. Compound feeds can be complete feeds that provide all the daily required nutrients, concentrates that provide a part of the ration (protein, energy) or supplements that only provide additional micronutrients, such as minerals and vitamins.

The main ingredients used in compound feed are the feed grains, which include corn, soybeans, sorghum, wheat, oats, and barley.

Suitably a premix as referred to herein may be a composition composed of microingredients such as vitamins, minerals, chemical preservatives, antibiotics, fermentation products, and other essential ingredients. Premixes are usually compositions suitable for blending into commercial rations.

Any feedstuff of the present invention may comprise one or more feed materials selected from the group comprising a) cereals, such as small grains (e.g., wheat, barley, rye, oats and combinations thereof) and/or large grains such as maize or sorghum; b) by products from cereals, such as corn gluten meal, wet-cake (particularly corn based wet-cake), Distillers Dried Grain (DDG) (particularly corn based Distillers Dried Grain (cDDG)), Distillers Dried Grain Solubles (DDGS) (particularly corn based Distillers Dried Grain Solubles (cDDGS)), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

A feedstuff of the present invention may contain at least 10%, at least 20%, at least 30% or at least 50% by weight corn and soybean meal or corn and full fat soy, or wheat meal or sunflower meal.

A feedstuff of the present invention may contain between about 0 to about 40% corn DDGS. If the feedstuff contains any corn DDGS it may contain between about 5 to about 40% corn DDGS. For poultry—where corn DDGS is present the feedstuff on average may contain between about 7 to 15% corn DDGS. For swine (pigs)—where corn DDGS is present the feedstuff may contain on average 5 to 40% corn DDGS.

A feedstuff of the present invention may contain corn as a single grain, in which case the feedstuff may comprise between about 35% to about 80% corn.

In the present invention the feed may be one or more of the following: a compound feed and premix, including pellets, nuts or (cattle) cake; a crop or crop residue: corn, soybeans, sorghum, oats, barley, copra, chaff, sugar beet waste; fish meal; meat and bone meal; molasses; oil cake and press cake; oligosaccharides; conserved forage plants: silage; seaweed; seeds and grains, either whole or prepared by crushing, milling etc.; sprouted grains and legumes; yeast extract.

The term feed in the present invention also encompasses in some embodiments pet food. A pet food is plant or animal material intended for consumption by pets, such as dog food or cat food. Pet food, such as dog and cat food, may be either in a dry form, such as kibble for dogs, or wet canned form. Cat food may contain the amino acid taurine.

The term feed in the present invention also encompasses in some embodiments fish food. A fish food normally contains macro nutrients, trace elements and vitamins necessary to keep captive fish in good health. Fish food may be in the form of a flake, pellet or tablet. Pelleted forms, some of which sink rapidly, are often used for larger fish or bottom feeding species.

Some fish foods also contain additives, such as beta carotene or sex hormones, to artificially enhance the color of ornamental fish.

The term feed in the present invention also encompasses in some embodiment bird food. Bird food includes food that is used both in birdfeeders and to feed pet birds. Typically bird food comprises of a variety of seeds, but may also encompass suet (beef or mutton fat).

As used herein the term "contacted" refers to the indirect or direct application of the composition of the present invention to the product (e.g. the feed). Examples of the application methods which may be used, include, but are not limited to, treating the product in a material comprising the feed additive composition, direct application by mixing the feed additive composition with the product, spraying the feed additive composition onto the product surface or dipping the product into a preparation of the feed additive composition.

In one embodiment the feed additive composition of the present invention is preferably admixed with the product (e.g. feedstuff). Alternatively, the feed additive composition may be included in the emulsion or raw ingredients of a feedstuff.

For some applications, it is important that the composition is made available on or to the surface of a product to be affected/treated. This allows the composition to impart one or more of the following favourable characteristics: performance benefits.

The feed additive compositions of the present invention may be applied to intersperse, coat and/or impregnate a product (e.g. feedstuff or raw ingredients of a feedstuff) with a controlled amount of DFM and enzyme(s).

The DFM and enzyme(s) may be used simultaneously (e.g. when they are in admixture together or even when they are delivered by different routes) or sequentially (e.g. they may be delivered by different routes). In one embodiment preferably the DFM and enzyme(s) are applied simultaneously. Preferably the DFM and enzyme(s) are admixed prior to being delivered to a feedstuff or to a raw ingredient of a feedstuff.

The DFM in feed additive compositions according to the present invention—can be added in suitable concentrations—such as for example in concentrations in the final feed product which offer a daily dose of between about $2 \times 10^5$ CFU to about $2 \times 10^{11}$ CFU, suitably between about $2 \times 10^6$ to about $1 \times 10^{10}$, suitably between about $3.75 \times 10^7$ CFU to about $1 \times 10^{10}$ CFU. Preferably, the feed additive composition of the present invention will be thermally stable to heat treatment up to about 70° C.; up to about 85° C.; or up to about 95° C. The heat treatment may be performed for up to about 1 minute; up to about 5 minutes; up to about 10 minutes; up to about 30 minutes; up to about 60 minutes. The term thermally stable means that at least about 75% of the enzyme components and/or DFM that were present/active in the additive before heating to the specified temperature are still present/active after it cools to room temperature. Preferably, at least about 80% of the enzyme components and/or DFM that were present and active in the additive before heating to the specified temperature are still present and active after it cools to room temperature.

In a particularly preferred embodiment the feed additive composition is homogenized to produce a powder.

In an alternative preferred embodiment, the feed additive composition is formulated to granules as described in WO2007/044968 (referred to as TPT granules) incorporated herein by reference.

In another preferred embodiment when the feed additive composition is formulated into granules the granules comprise a hydrated barrier salt coated over the protein core. The advantage of such salt coating is improved thermo-tolerance, improved storage stability and protection against other feed additives otherwise having adverse effect on the enzyme and/or DFM.

Preferably, the salt used for the salt coating has a water activity greater than 0.25 or constant humidity greater than 60% at 20° C.

Preferably, the salt coating comprises a $Na_2SO_4$.

The method of preparing a feed additive composition may also comprise the further step of pelleting the powder. The powder may be mixed with other components known in the art. The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes and even hours. Such as 5 seconds, 10 seconds, 15 seconds, 30 seconds, 1 minutes, 2 minutes, 5 minutes, 10 minutes, 15 minutes, 30 minutes and 1 hour.

It will be understood that the feed additive composition of the present invention is suitable for addition to any appropriate feed material.

As used herein, the term feed material refers to the basic feed material to be consumed by an animal. It will be further understood that this may comprise, for example, at least one or more unprocessed grains, and/or processed plant and/or animal material such as soybean meal or bone meal.

As used herein, the term "feedstuff" refers to a feed material to which one or more feed additive compositions have been added.

It will be understood by the skilled person that different animals require different feedstuffs, and even the same animal may require different feedstuffs, depending upon the purpose for which the animal is reared.

Preferably, the feedstuff may comprise feed materials comprising maize or corn, wheat, barley, triticale, rye, rice, tapioca, sorghum, and/or any of the by-products, as well as protein rich components like soybean mean, rape seed meal, canola meal, cotton seed meal, sunflower seed mean, animal-by-product meals and mixtures thereof. More preferably, the feedstuff may comprise animal fats and/or vegetable oils.

Optionally, the feedstuff may also contain additional minerals such as, for example, calcium and/or additional vitamins.

Preferably, the feedstuff is a corn soybean meal mix.

In one embodiment, preferably the feed is not pet food.

In another aspect there is provided a method for producing a feedstuff. Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting—in particular by suitable techniques that may include at least the use of steam.

The feedstuff may be a feedstuff for a monogastric animal, such as poultry (for example, broiler, layer, broiler breeders, turkey, duck, geese, water fowl), swine (all age categories), a pet (for example dogs, cats) or fish, preferably the feedstuff is for poultry.

In one embodiment the feedstuff is not for a layer.

By way of example only a feedstuff for chickens, e.g. broiler chickens may be comprised of one or more of the ingredients listed in the table below, for example in the % ages given in the table below:

| Ingredients | Starter (%) | Finisher (%) |
| --- | --- | --- |
| Maize | 46.2 | 46.7 |
| Wheat Middlings | 6.7 | 10.0 |
| Maize DDGS | 7.0 | 7.0 |
| Soyabean Meal 48% CP | 32.8 | 26.2 |
| An/Veg Fat blend | 3.0 | 5.8 |
| L-Lysine HCl | 0.3 | 0.3 |
| DL-methionine | 0.3 | 0.3 |
| L-threonine | 0.1 | 0.1 |
| Salt | 0.3 | 0.4 |
| Limestone | 1.1 | 1.1 |
| Dicalcium Phosphate | 1.2 | 1.2 |
| Poultry Vitamins and Micro-minerals | 0.3 | 0.3 |

By way of example only the diet specification for chickens, such as broiler chickens, may be as set out in the Table below:

| Diet specification | | |
| --- | --- | --- |
| Crude Protein (%) | 23.00 | 20.40 |
| Metabolizable Energy Poultry (kcal/kg) | 2950 | 3100 |
| Calcium (%) | 0.85 | 0.85 |
| Available Phosphorus (%) | 0.38 | 0.38 |
| Sodium (%) | 0.18 | 0.19 |
| Dig. Lysine (%) | 1.21 | 1.07 |
| Dig. Methionine (%) | 0.62 | 0.57 |
| Dig. Methionine + Cysteine (%) | 0.86 | 0.78 |
| Dig. Threonine (%) | 0.76 | 0.68 |

By way of example only a feedstuff laying hens may be comprises of one or more of the ingredients listed in the table below, for example in the % ages given in the table below:

| Ingredient | Laying phase (%) |
| --- | --- |
| Maize | 10.0 |
| Wheat | 53.6 |
| Maize DDGS | 5.0 |
| Soybean Meal 48% CP | 14.9 |
| Wheat Middlings | 3.0 |
| Soybean Oil | 1.8 |
| L-Lysine HCl | 0.2 |
| DL-methionine | 0.2 |
| L-threonine | 0.1 |
| Salt | 0.3 |
| Dicalcium Phosphate | 1.6 |
| Limestone | 8.9 |
| Poultry Vitamins and Micro-minerals | 0.6 |

By way of example only the diet specification for laying hens may be as set out in the Table below:

| Diet specification | |
| --- | --- |
| Crude Protein (%) | 16.10 |
| Metabolizable Energy Poultry (kcal/kg) | 2700 |
| Lysine (%) | 0.85 |
| Methionine (%) | 0.42 |
| Methionine + Cysteine (%) | 0.71 |
| Threonine (%) | 0.60 |
| Calcium (%) | 3.85 |
| Available Phosphorus (%) | 0.42 |
| Sodium (%) | 0.16 |

By way of example only a feedstuff for turkeys may be comprises of one or more of the ingredients listed in the table below, for example in the % ages given in the table below:

| Ingredient | Phase 1 (%) | Phase 2 (%) | Phase 3 (%) | Phase 4 (%) |
|---|---|---|---|---|
| Wheat | 33.6 | 42.3 | 52.4 | 61.6 |
| Maize DDGS | 7.0 | 7.0 | 7.0 | 7.0 |
| Soyabean Meal 48% CP | 44.6 | 36.6 | 27.2 | 19.2 |
| Rapeseed Meal | 4.0 | 4.0 | 4.0 | 4.0 |
| Soyabean Oil | 4.4 | 4.2 | 3.9 | 3.6 |
| L-Lysine HCl | 0.5 | 0.5 | 0.4 | 0.4 |
| DL-methionine | 0.4 | 0.4 | 0.3 | 0.2 |
| L-threonine | 0.2 | 0.2 | 0.1 | 0.1 |
| Salt | 0.3 | 0.3 | 0.3 | 0.3 |
| Limestone | 1.0 | 1.1 | 1.1 | 1.0 |
| Dicalcium Phosphate | 3.5 | 3.0 | 2.7 | 2.0 |
| Poultry Vitamins and Micro-minerals | 0.4 | 0.4 | 0.4 | 0.4 |

By way of example only the diet specification for turkeys may be as set out in the Table below:

| Diet specification | | | | |
|---|---|---|---|---|
| Crude Protein (%) | 29.35 | 26.37 | 22.93 | 20.00 |
| Metabolizable Energy Poultry (kcal/kg) | 2.850 | 2.900 | 2.950 | 3.001 |
| Calcium (%) | 1.43 | 1.33 | 1.22 | 1.02 |
| Available Phosphorus (%) | 0.80 | 0.71 | 0.65 | 0.53 |
| Sodium (%) | 0.16 | 0.17 | 0.17 | 0.17 |
| Dig. Lysine (%) | 1.77 | 1.53 | 1.27 | 1.04 |
| Dig. Methionine (%) | 0.79 | 0.71 | 0.62 | 0.48 |
| Dig. Methionine + Cysteine (%) | 1.12 | 1.02 | 0.90 | 0.74 |
| Dig. Threonine (%) | 1.03 | 0.89 | 0.73 | 0.59 |

By way of example only a feedstuff for piglets may be comprises of one or more of the ingredients listed in the table below, for example in the % ages given in the table below:

| Ingredient | Phase 1 (%) | Phase 2 (%) |
|---|---|---|
| Maize | 20.0 | 7.0 |
| Wheat | 25.9 | 46.6 |
| Rye | 4.0 | 10.0 |
| Wheat middlings | 4.0 | 4.0 |
| Maize DDGS | 6.0 | 8.0 |
| Soyabean Meal 48% CP | 25.7 | 19.9 |
| Dried Whey | 10.0 | 0.0 |
| Soyabean Oil | 1.0 | 0.7 |
| L-Lysine HCl | 0.4 | 0.5 |
| DL-methionine | 0.2 | 0.2 |
| L-threonine | 0.1 | 0.2 |
| L-tryptophan | 0.03 | 0.04 |
| Limestone | 0.6 | 0.7 |
| Dicalcium Phosphate | 1.6 | 1.6 |
| Swine Vitamins and Micro-minerals | 0.2 | 0.2 |
| Salt | 0.2 | 0.4 |

By way of example only the diet specification for piglets may be as set out in the Table below:

| Diet specification | | |
|---|---|---|
| Crude Protein (%) | 21.50 | 20.00 |
| Swine Digestible Energy (kcal/kg) | 3380 | 3320 |
| Swine Net Energy (kcal/kg) | 2270 | 2230 |
| Calcium (%) | 0.80 | 0.75 |
| Digestible Phosphorus (%) | 0.40 | 0.35 |
| Sodium (%) | 0.20 | 0.20 |
| Dig. Lysine (%) | 1.23 | 1.14 |
| Dig. Methionine (%) | 0.49 | 0.44 |
| Dig. Methionine + Cysteine (%) | 0.74 | 0.68 |
| Dig. Threonine (%) | 0.80 | 0.74 |

By way of example only a feedstuff for grower/finisher pigs may be comprises of one or more of the ingredients listed in the table below, for example in the % ages given in the table below:

| Ingredient | Grower/Finisher (%) |
|---|---|
| Maize | 27.5 |
| Soyabean Meal 48% CP | 15.4 |
| Maize DDGS | 20.0 |
| Wheat bran | 11.1 |
| Rice bran | 12.0 |
| Canola seed meal | 10.0 |
| Limestone | 1.6 |
| Dicalcium phosphate | 0.01 |
| Salt | 0.4 |
| Swine Vitamins and Micro-minerals | 0.3 |
| Lysine-HCl | 0.2 |
| Vegetable oil | 0.5 |

By way of example only the diet specification for grower/finisher pigs may be as set out in the Table below:

| Diet specification | |
|---|---|
| Crude Protein (%) | 22.60 |
| Swine Metabolizable Energy (kcal/kg) | 3030 |
| Calcium (%) | 0.75 |
| Available Phosphorus (%) | 0.29 |
| Digestible Lysine (%) | 1.01 |
| Dig. Methionine + Cysteine (%) | 0.73 |
| Digestible Threonine (%) | 0.66 |

Forms

The feed additive composition of the present invention and other components and/or the feedstuff comprising same may be used in any suitable form.

The feed additive composition of the present invention may be used in the form of solid or liquid preparations or alternatives thereof. Examples of solid preparations include powders, pastes, boluses, capsules, pellets, tablets, dusts, and granules which may be wettable, spray-dried or freeze-dried. Examples of liquid preparations include, but are not limited to, aqueous, organic or aqueous-organic solutions, suspensions and emulsions.

In some applications, DFM or feed additive compositions of the present invention may be mixed with feed or administered in the drinking water. In one embodiment the dosage range for inclusion into water is about $1 \times 10^3$ CFU/animal/day to about $1 \times 10^{10}$ CFU/animal/day, and more preferably about $1 \times 10^7$ CFU/animal/day.

Suitable examples of forms include one or more of: powders, pastes, boluses, pellets, tablets, pills, capsules, ovules, solutions or suspensions, which may contain flavouring or colouring agents, for immediate-, delayed-, modified-, sustained-, pulsed- or controlled-release applications.

By way of example, if the composition of the present invention is used in a solid, e.g. pelleted form, it may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Preferred excipients for the forms include lactose, starch, a cellulose, milk sugar or high molecular weight polyethylene glycols.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

Non-hydroscopic whey is often used as a carrier for DFMs (particularly bacterial DFMs) and is a good medium to initiate growth.

Bacterial DFM containing pastes may be formulated with vegetable oil and inert gelling ingredients.

Fungal products may be formulated with grain by-products as carriers.

In one embodiment preferably the feed additive composition according to the present invention is not in the form of a microparticle system, such as the microparticle system taught in WO2005/123034.

Dosing

The DFM and/or feed additive composition according to the present invention may be designed for one-time dosing or may be designed for feeding on a daily basis.

The optimum amount of the composition (and each component therein) to be used in the combination of the present invention will depend on the product to be treated and/or the method of contacting the product with the composition and/or the intended use for the same. The amount of DFM and enzyme(s) used in the compositions should be a sufficient amount to be effective and to remain sufficiently effective in improving the performance of the animal fed feed products containing said composition.

This length of time for effectiveness should extend up to at least the time of utilisation of the product (e.g. feed additive composition or feed containing same).

The ratio of DFM to enzyme in the feed can be in the ranges given below:

DFM:phytase (CFU/FTU): In range from $2.5 \times 10^3$ CFU DFM: 1 FTU enzyme to $6.7 \times 10^6$ CFU:1 FTU enzyme; preferably in the range from $3.8 \times 10^3$ CFU DFM: 1 FTU enzyme to $2.0 \times 10^5$ CFU:1 FTU enzyme.

In one embodiment preferably the feedstuff comprises the following:
a phytase at (at least) 1500 FTU/kg of feed; and
Envivo Pro (DFM) at at least $7.5 \times 10^4$ CFU/g to $3.0 \times 10^5$ CFU/g of feed.

In one embodiment preferably the feedstuff comprises the following:
a phytase at (at least) 2000 FTU/kg of feed; and
Envivo Pro (DFM) at $7.5 \times 10^4$ CFU/g to $3.0 \times 10^5$ CFU/g of feed.

In one embodiment preferably the feedstuff comprises the following:
a phytase at (at least) 3000 FTU/kg of feed; and
Envivo Pro (DFM) at $7.5 \times 10^4$ CFU/g to $3.0 \times 10^5$ CFU/g of feed.

In one embodiment preferably the feedstuff comprises the following:
a phytase at (at least) 1500 FTU/kg of feed; and
DFM at at least $5 \times 10^4$ CFU/g to $1 \times 10^7$ CFU/g of feed.

In one embodiment preferably the feedstuff comprises the following:
a phytase at (at least) 2000 FTU/kg of feed; and
DFM at at least $5 \times 10^4$ CFU/g to $1 \times 10^7$ CFU/g of feed.

In one embodiment preferably the feedstuff comprises the following:
a phytase at (at least) 3000 FTU/kg of feed; and
DFM at at least $5 \times 10^4$ CFU/g to $1 \times 10^7$ CFU/g of feed.

In another embodiment the feedstuff comprises the following:

In a preferred embodiment the feed additive composition comprises sufficient enzyme and DFMs to dose the feedstuff as follows:
a phytase at (at least) 1500 FTU/kg (e.g. at (at least) 2000 FTU/kg) of feed; and
Envivo Pro (DFM) at 75,000 CFU/g to 150,000 CFU/g of feed.

In a preferred embodiment the feed additive composition comprises sufficient enzyme and DFMs to dose the feedstuff as follows:
a phytase at (at least) 1500 FTU/kg (e.g. at (at least) 2000 FTU/kg) of feed; and
Envivo Pro (DFM) at 37,500 CFU/g to 75,000 CFU/g of feed.

Combination with Other Components

The DFM and enzyme(s) for use in the present invention may be used in combination with other components. Thus, the present invention also relates to combinations. The DFM in combination with a phytase may be referred to herein as "the feed additive composition of the present invention".

The combination of the present invention comprises the feed additive composition of the present invention (or one or more of the constituents thereof) and another component which is suitable for animal consumption and is capable of providing a medical or physiological benefit to the consumer.

In one embodiment preferably the "another component" is not a further enzyme or a further DFM.

The components may be prebiotics. Prebiotics are typically non-digestible carbohydrate (oligo- or polysaccharides) or a sugar alcohol which is not degraded or absorbed in the upper digestive tract. Known prebiotics used in commercial products and useful in accordance with the present invention include inulin (fructo-oligosaccharide, or FOS) and transgalacto-oligosaccharides (GOS or TOS). Suitable prebiotics include palatinoseoligosaccharide, soybean oligosaccharide, alginate, xanthan, pectin, locust bean gum (LBG), inulin, guar gum, galacto-oligosaccharide (GOS), fructo-oligosaccharide (FOS), non-degradable starch, lactosaccharose, lactulose, lactitol, maltitol, maltodextrin, polydextrose (i.e. Litesse®), lactitol, lactosucrose, soybean oligosaccharides, palatinose, isomalto-oligosaccharides, gluco-oligosaccharides and xylo-oligosaccharides, pectin fragments, dietary fibres, mannan-oligosaccharides.

Dietary fibres may include non-starch polysaccharides, such as arabinoxylans, cellulose and many other plant components, such as resistant dextrins, inulin, lignin, waxes, chitins, pectins, beta-glucans and oligosaccharides.

In one embodiment the present invention relates to the combination of the feed additive composition according to the present invention (or one or more of the constituents thereof) with a prebiotic. In another embodiment the present invention relates to a feed additive composition comprising (or consisting essentially of or consisting of) a DFM in combination with a high dosage of phytase, and a prebiotic.

The prebiotic may be administered simultaneously with (e.g. in admixture together with or delivered simultaneously by the same or different routes) or sequentially to (e.g. by the same or different routes) the feed additive composition (or constituents thereof) according to the present invention.

Other components of the combinations of the present invention include polydextrose, such as Litesse®, and/or a maltodextrin and/or lactitol. These other components may be optionally added to the feed additive composition to assist the drying process and help the survival of DFM.

Further examples of other suitable components include one or more of: thickeners, gelling agents, emulsifiers, binders, crystal modifiers, sweeteners (including artificial sweeteners), rheology modifiers, stabilisers, anti-oxidants, dyes, enzymes, carriers, vehicles, excipients, diluents, lubricating agents, flavouring agents, colouring matter, suspending agents, disintegrants, granulation binders etc. These other components may be natural. These other components may be prepared by use of chemical and/or enzymatic techniques.

In one preferred embodiment the DFM and/or enzyme for use in the present invention may be used in combination with one or more lipids.

For example, the DFM and/or enzyme for use in the present invention may be used in combination with one or more lipid micelles. The lipid micelle may be a simple lipid micelle or a complex lipid micelle.

The lipid micelle may be an aggregate of orientated molecules of amphipathic substances, such as a lipid and/or an oil.

As used herein the term "thickener or gelling agent" refers to a product that prevents separation by slowing or preventing the movement of particles, either droplets of immiscible liquids, air or insoluble solids. Thickening occurs when individual hydrated molecules cause an increase in viscosity, slowing the separation. Gelation occurs when the hydrated molecules link to form a three-dimensional network that traps the particles, thereby immobilising them.

The term "stabiliser" as used here is defined as an ingredient or combination of ingredients that keeps a product (e.g. a feed product) from changing over time.

The term "emulsifier" as used herein refers to an ingredient (e.g. a feed ingredient) that prevents the separation of emulsions. Emulsions are two immiscible substances, one present in droplet form, contained within the other. Emulsions can consist of oil-in-water, where the droplet or dispersed phase is oil and the continuous phase is water; or water-in-oil, where the water becomes the dispersed phase and the continuous phase is oil. Foams, which are gas-in-liquid, and suspensions, which are solid-in-liquid, can also be stabilised through the use of emulsifiers.

As used herein the term "binder" refers to an ingredient (e.g. a feed ingredient) that binds the product together through a physical or chemical reaction. During "gelation" for instance, water is absorbed, providing a binding effect. However, binders can absorb other liquids, such as oils, holding them within the product. In the context of the present invention binders would typically be used in solid or low-moisture products for instance baking products: pastries, doughnuts, bread and others.

"Carriers" or "vehicles" mean materials suitable for administration of the DFM and/or enzymes and include any such material known in the art such as, for example, any liquid, gel, solvent, liquid diluent, solubilizer, or the like, which is non-toxic and which does not interact with any components of the composition in a deleterious manner.

The present invention provides a method for preparing a feed additive composition comprising admixing a DFM, and a phytase with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

Examples of excipients include one or more of: microcrystalline cellulose and other celluloses, lactose, sodium citrate, calcium carbonate, dibasic calcium phosphate, glycine, starch, milk sugar and high molecular weight polyethylene glycols.

Examples of disintegrants include one or more of: starch (preferably corn, potato or tapioca starch), sodium starch glycollate, croscarmellose sodium and certain complex silicates.

Examples of granulation binders include one or more of: polyvinylpyrrolidone, hydroxypropylmethylcellulose (HPMC), hydroxypropylcellulose (HPC), sucrose, maltose, gelatin and acacia.

Examples of lubricating agents include one or more of: magnesium stearate, stearic acid, glyceryl behenate and talc.

Examples of diluents include one or more of: water, ethanol, propylene glycol and glycerin, and combinations thereof.

The other components may be used simultaneously (e.g. when they are in admixture together or even when they are delivered by different routes) or sequentially (e.g. they may be delivered by different routes).

Preferably, when the feed additive composition of the present invention is admixed with another component(s), the DFM remains viable.

In one embodiment preferably the feed additive composition according to the present invention does not comprise chromium or organic chromium Concentrates The DFMs for use in the present invention may be in the form of concentrates. Typically these concentrates comprise a substantially high concentration of a DFM.

Feed additive compositions according to the present invention may have a content of viable cells (colony forming units, CFUs) which is in the range of at least $10^4$ CFU/g (suitably including at least $10^5$ CFU/g, such as at least $10^6$ CFU/g, e.g. at least $10^7$ CFU/g, at least $10^8$ CFU/g) to about $10^{10}$ CFU/g (or even about $10^{11}$ CFU/g or about $10^{12}$ CFU/g).

When the DFM is in the form of a concentrate the feed additive compositions according to the present invention may have a content of viable cells in the range of at least $10^9$ CFU/g to about $10^{12}$ CFU/g, preferably at least $10^{10}$ CFU/g to about $10^{12}$ CFU/g.

Powders, granules and liquid compositions in the form of concentrates may be diluted with water or resuspended in water or other suitable diluents, for example, an appropriate growth medium such as milk or mineral or vegetable oils, to give compositions ready for use.

The DFM or feed additive composition of the present invention or the combinations of the present invention in the form of concentrates may be prepared according to methods known in the art.

In one aspect of the present invention the enzymes or feed is contacted by a composition in a concentrated form.

The compositions of the present invention may be spray-dried or freeze-dried by methods known in the art.

Typical processes for making particles using a spray drying process involve a solid material which is dissolved in an appropriate solvent (e.g. a culture of a DFM in a fermentation medium). Alternatively, the material can be suspended or emulsified in a non-solvent to form a suspension or emulsion. Other ingredients (as discussed above) or components such as anti-microbial agents, stabilising agents, dyes and agents assisting with the drying process may optionally be added at this stage.

The solution then is atomised to form a fine mist of droplets. The droplets immediately enter a drying chamber where they contact a drying gas. The solvent is evaporated from the droplets into the drying gas to solidify the droplets, thereby forming particles. The particles are then separated from the drying gas and collected.

Subject

The term "subject", as used herein, means an animal that is to be or has been administered with a feed additive composition according to the present invention or a feedstuff comprising said feed additive composition according to the present invention.

The term "subject", as used herein, means an animal.

In one embodiment, the subject is a mammal, bird, fish or crustacean including for example livestock or a domesticated animal (e.g. a pet).

In one embodiment the "subject" is livestock.

The term "livestock", as used herein refers to any farmed animal. Preferably, livestock is one or more of ruminants such as cattle (e.g. cows or bulls (including calves)), monogastric animals such as poultry (including broilers, chickens and turkeys), pigs (including piglets), birds, aquatic animals such as fish, agastric fish, gastric fish, freshwater fish such as salmon, cod, trout and carp, e.g. koi carp, marine fish such as sea bass, and crustaceans such as shrimps, mussels and scallops), horses (including race horses), sheep (including lambs).

In another embodiment the "subject" is a domesticated animal or pet or an animal maintained in a zoological environment.

The term "domesticated animal or pet or animal maintained in a zoological environment" as used herein refers to any relevant animal including canines (e.g. dogs), felines (e.g. cats), rodents (e.g. guinea pigs, rats, mice), birds, fish (including freshwater fish and marine fish), and horses.

In one embodiment the subject may be challenged by an enteric pathogen.

By way of example a subject may have one or more enteric pathogens present in its gut or digestive tract. For example a subject may have one or more enteric pathogens in its gut or digestive tract at a level which:

i) results in loss of performance of the animal and/or
ii) is at clinically relevant levels; or
iii) is at sub-clinical levels.

The enteric pathogen may be *Clostridium perfringens* for example.

Performance

As used herein, "animal performance" may be determined by the feed efficiency and/or weight gain of the animal and/or by the feed conversion ratio and/or by the digestibility of a nutrient in a feed (e.g. amino acid digestibility) and/or digestible energy or metabolizable energy in a feed and/or by nitrogen retention and/or by animals ability to avoid the negative effects of necrotic enteritis and/or by the immune response of the subject.

Preferably "animal performance" is determined by feed efficiency and/or weight gain of the animal and/or by the feed conversion ratio.

By "improved animal performance" it is meant that there is increased feed efficiency, and/or increased weight gain and/or reduced feed conversion ratio and/or improved digestibility of nutrients or energy in a feed and/or by improved nitrogen retention and/or by improved ability to avoid the negative effects of necrotic enteritis and/or by an improved immune response in the subject resulting from the use of feed additive composition of the present invention in feed in comparison to feed which does not comprise said feed additive composition.

Preferably, by "improved animal performance" it is meant that there is increased feed efficiency and/or increased weight gain and/or reduced feed conversion ratio.

As used herein, the term "feed efficiency" refers to the amount of weight gain in an animal that occurs when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Feed Conversion Ratio (FCR)

As used herein, the term "feed conversion ratio" refers to the amount of feed fed to an animal to increase the weight of the animal by a specified amount.

An improved feed conversion ratio means a lower feed conversion ratio.

By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Nutrient Digestibility

Nutrient digestibility as used herein means the fraction of a nutrient that disappears from the gastro-intestinal tract or a specified segment of the gastro-intestinal tract, e.g. the small intestine. Nutrient digestibility may be measured as the difference between what is administered to the subject and what comes out in the faeces of the subject, or between what is administered to the subject and what remains in the digesta on a specified segment of the gastro intestinal tract, e.g. the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed.

Nutrient digestibility as used herein encompasses starch digestibility, fat digestibility, protein digestibility, and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g. the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

Nitrogen Retention

Nitrogen retention as used herein means as subject's ability to retain nitrogen from the diet as body mass. A negative nitrogen balance occurs when the excretion of nitrogen exceeds the daily intake and is often seen when the muscle is being lost. A positive nitrogen balance is often associated with muscle growth, particularly in growing animals.

Nitrogen retention may be measured as the difference between the intake of nitrogen and the excreted nitrogen by means of the total collection of excreta and urine during a period of time.

It is understood that excreted nitrogen includes undigested protein from the feed, endogenous proteinaceous secretions, microbial protein, and urinary nitrogen.

Survival

The term survival as used herein means the number of subject remaining alive. The term "improved survival" may be another way of saying "reduced mortality".

Carcass Yield and Meat Yield

The term carcass yield as used herein means the amount of carcass as a proportion of the live body weight, after a commercial or experimental process of slaughter. The term carcass means the body of an animal that has been slaughtered for food, with the head, entrails, part of the limbs, and feathers or skin removed. The term meat yield as used herein means the amount of edible meat as a proportion of the live body weight, or the amount of a specified meat cut as a proportion of the live body weight.

Weight Gain

The present invention further provides a method of increasing weight gain in a subject, e.g. poultry or swine, comprising feeding said subject a feedstuff comprising a feed additive composition according to the present invention.

An "increased weight gain" refers to an animal having increased body weight on being fed feed comprising a feed additive composition compared with an animal being fed a feed without said feed additive composition being present.

The increase in weight gain may be at least 0.5%, at least 1%, at least 2%, at least 3%, at least 5%, at least 10%, at least 12%, at least 15%, at least 20% or at least 30%. In some embodiments the improvement may be at least 50% or at least 100%.

The increase in weight gain may be in respect to a control in which the feed used does not comprise a DFM and high dosage (i.e. >1500 FTU/kg feed) phytase. In another aspect the increase in weight gain may be with respect to the use of a feed comprising another phytase wherein the phytase is used in a low dose e.g. <1000 FTU/kg feed.

Clinical or Subclinical Intestinal Disease Challenge

In one embodiment a clinical or subclinical intestinal disease challenge is present in the subject.

In one embodiment the clinical or subclinical intestinal disease challenge may be caused by any pathogen or any pathogenic bacteria, such as *Clostridium perfringens* or *E. coli*.

The term "clinical disease" means a stage in the history of a pathologic condition that begins with anatomic or physiologic changes that are sufficient to produce recognizable signs and symptoms of a disease.

The term "subclinical disease" means or relates to a stage in the course of a disease before the symptoms are first noted.

The intestinal disease may be any intestinal infection which the subject can suffer from.

In one example the intestinal disease may be caused by pathogenic organisms, such as pathogenic bacteria.

In one embodiment the intestinal disease may be caused by one or more of the following organisms: pathogenic *Clostridium* spp, such as *Clostridium perfringens* and/or *Clostridium difficile*, and/or *E. coli* and/or *Salmonella* spp and/or *Campylobacter* spp.

In one embodiment the intestinal disease may be caused by one or more of the following pathogens: *Clostridium perfringens* and/or *Clostridium difficile* and/or *E. coli*, preferably *Clostridium perfringens* and/or *Clostridium difficile*, more preferably *Clostridium perfringens*.

Necrotic Enteritis

Necrotic enteritis is an acute or chronic enterotoxemia seen in chickens, turkeys and ducks worldwide, caused by *Clostridium perfringens*. Necrotic enteritis is often characterised by a fibrino-necrotic enteritis, usually of the mid-small intestine. Mortality may be 5-50%, usually around 10%. Infection occurs by faecal-oral transmission. Spores of the causative organism are highly resistant. Predisposing factors include coccidiosis/coccidiasis, diet (high protein), in ducks possibly heavy strains, high viscosity diets (often associated with high rye and wheat inclusions in the diet), contaminated feed and/or water, other debilitating diseases.

The present invention relates to increasing the subject's resistance to necrotic enteritis. In other words, the present invention relates to avoiding or reducing the negative effect of necrotic enteritis.

The term "resistance to" as used herein may encompasses the term "tolerance of". Therefore in one embodiment the subject may not be resistant to necrotic enteritis but the subject may be able to tolerate the necrotic enteritis, i.e. without negative effects on performance of the subject.

In one embodiment the present invention relates to a feed additive composition according to the present invention for treating or preventing necrotic enteritis in a subject. Typically the subject will be one which has been or will be challenged with *Clostridium perfringens* and/or *Eimeria* species. Such challenge may come from the environment or the application of live microorganisms in the feed or drinking water, e.g. when live coccidia vaccines are used.

In another embodiment the present invention relates to a feed additive composition for preventing and/or treating coccidiosis in a subject.

The present invention yet further provides a method of preventing and/or treating necrotic enteritis and/or coccidiosis wherein an effective amount of a feed additive composition according to the present invention is administered to a subject.

Immune Response

Immune response as used herein means one of the multiple ways in which DFMs modulate the immune system of animals, including increased antibody production, up-regulation of cell mediated immunity, up-regulation of pro-inflammatory cytokines, and augmented toll-like receptor signalling. It is understood that immuno-stimulation of the gastro intestinal tract by DFMs may be advantageous to protect the host against disease, and that immuno-suppression of the gastro intestinal tract may be advantageous to the host because less nutrients and energy are used to support the immune function.

Preferably the immune response is a cellular immune response.

Preferably immune response is measure by looking at immune markers.

Pathogenic Bacteria

The term pathogenic bacteria as used herein means for example toxigenic clostridia species, e.g. *Clostridium perfringens* and/or *E. coli* and/or *Salmonella* spp and/or *Campylobacter* spp. In one embodiment the pathogenic bacteria may be Avian pathogenic *E. coli* species.

The present invention may reduce populations of pathogenic bacteria in the gastrointestinal tract of a subject.

Nutrient Excretion

In one embodiment the present invention relates to reducing nutrient excretion in manure. This has positive effects on reducing environmental hazards. For example, in a preferred embodiment the present invention relates to reducing nitrogen and/or phosphorus content in the subject's manure. This, therefore, reduces the amount of nitrogen and/or phosphorus in the environment, which can be beneficial.

Probiotic

For some applications, it is believed that the DFM in the composition of the present invention can exert a probiotic culture effect. It is also within the scope of the present invention to add to the composition of the present invention further probiotic and/or prebiotics.

Here, a prebiotic is:

"a non-digestible food ingredient that beneficially affects the host by selectively stimulating the growth and/or the activity of one or a limited number of beneficial bacteria".

The term "probiotic culture" as used herein defines live microorganisms (including bacteria or yeasts for example) which, when for example ingested or locally applied in sufficient numbers, beneficially affects the host organism, i.e. by conferring one or more demonstrable health benefits on the host organism. Probiotics may improve the microbial balance in one or more mucosal surfaces. For example, the mucosal surface may be the intestine, the urinary tract, the respiratory tract or the skin. The term "probiotic" as used herein also encompasses live microorganisms that can stimulate the beneficial branches of the immune system and at the same time decrease the inflammatory reactions in a mucosal surface, for example the gut. Whilst there are no lower or upper limits for probiotic intake, it has been suggested that at least $10^6$-$10^{12}$, preferably at least $10^6$-$10^{19}$, preferably $10^8$-$10^9$, cfu as a daily dose will be effective to achieve the beneficial health effects in a subject.

Isolated

In one aspect, suitably the enzyme or DFM used in the present invention may be in an isolated form. The term "isolated" means that the enzyme or DFM is at least substantially free from at least one other component with which the enzyme or DFM is naturally associated in nature and as found in nature. The enzyme or DFM of the present invention may be provided in a form that is substantially free of one or more contaminants with which the substance might otherwise be associated. Thus, for example it may be substantially free of one or more potentially contaminating polypeptides and/or nucleic acid molecules.

Purified

In one aspect, preferably the enzyme and/or DFM according to the present invention is in a purified form. The term "purified" means that the enzyme and/or DFM is present at a high level. The enzyme and/or DFM is desirably the predominant component present in a composition. Preferably, it is present at a level of at least about 90%, or at least about 95% or at least about 98%, said level being determined on a dry weight/dry weight basis with respect to the total composition under consideration.

It is envisaged within the scope of the present invention that the embodiments of the invention can be combined such that combinations of any of the features described herein are included within the scope of the present invention. In particular, it is envisaged within the scope of the present invention that any of the therapeutic effects of the bacteria may be exhibited concomitantly.

The invention will now be described, by way of example only, with reference to the following Figures and Examples.

EXAMPLES

Example 1

Methods

A total of 1600 one-day-old Cobb male chicks are purchased from a commercial hatchery. At study initiation, fifty males are allocated to each treatment pen by blocks. The study consists of the following treatments (Table 1):

TABLE 1

Experimental design of Example 1.

| Dietary Treatment | *Clostridium perfringens* Challenge | Phyzyme XP[1] | DFM (CFU/g feed)[2] |
|---|---|---|---|
| 1 | No | 500 FTU/kg | None |
| 2 | Yes | 500 FTU/kg | None |
| 3 | Yes | 500 FTU/kg | Enviva Pro (7.5 × 10$^4$ CFU/g) |
| 4 | Yes | 3000 FTU/kg | Enviva Pro (7.5 × 10$^4$ CFU/g) |

[1]Phyzyme XP is a 6-phytase from *E. coli* provided by Danisco A/S.
[2]Enviva Pro ® is combination of *Bacillus subtilis* strains Bs2084, LSSAO1 and 15AP4, provided by Danisco A/S.

Bird weights by pen are recorded at study initiation, 23 d, 35 d, and termination (42 d). The pen is the unit of measure. Broiler diets are fed as crumbles (starter) or pellets (grower and finisher). Diets met or exceeded NRC standards (Table 2). The mixer is flushed to prevent cross contamination of diets. All treatment feeds are mixed using a Davis S-20 mixer and pelleted using a California Pellet Mill (cold pellet temperature 65-70 C). Samples are collected from each treatment diet from the beginning, middle, and end of each batch and blended together to confirm enzyme activities and Enviva Pro presence in feed.

TABLE 2

Experimental diet composition of Example 1.

|  | Starter (0-23 d) | Grower (23-35 d) | Finisher (35-42 d) |
|---|---|---|---|
| Ingredient (%) |  |  |  |
| Maize | 53.62 | 57.87 | 59.82 |
| Maize DDGS | 10.00 | 10.00 | 10.00 |
| Soybean Meal 49% CP | 26.93 | 23.97 | 21.36 |
| Ampro 55 | 5.00 | 5.00 | 5.00 |
| Soy oil | 2.07 | 0.91 | 1.74 |
| Lysine | 0.24 | 0.24 | 0.24 |
| DL-methionine | 0.21 | 0.19 | 0.18 |
| L-threonine | 0.01 | 0.01 | 0.01 |
| Salt | 0.30 | 0.34 | 0.35 |
| Limestone | 1.04 | 1.07 | 0.94 |
| Dicalcium phosphate | 0.26 | 0.11 | 0.02 |
| Vitamin and trace mineral premix | 0.33 | 0.33 | 0.33 |
| Calculated Nutrient Composition (%) |  |  |  |
| CP | 22.60 | 21.50 | 20.39 |
| Energy, kcal/kg | 3060 | 3025 | 3100 |
| Digestible lysine | 1.36 | 1.26 | 1.21 |
| Digestible methionine | 0.58 | 0.61 | 0.53 |
| Digestible threonine | 0.83 | 0.83 | 0.80 |

Birds receive feed ad-libitum appropriate to the treatment from day 0 to 42. Enzymes and Enviva Pro are provided by Danisco in the appropriate mixtures and levels for all experimental treatments. The pens are arranged within the facility to prevent direct contact in order to avoid contamination. A change from starter to grower occurred on day 23. Grower diet is replaced with the finisher diet on day 35. At each feed change, feeders are removed from pens by block, weighed back, emptied, and refilled with the appropriate treatment diet. On the final day of the study feed is weighed. Pens are checked daily for mortality. When a bird is culled or found dead, the date and removal weight (kg) are recorded. A gross necropsy is performed on all dead or culled birds to determine the sex and probable cause of death. Signs of Necrotic Enteritis are noted.

All pens had approximately 4 inches of built up litter with a coating of fresh pine shavings. All birds are spray vaccinated prior to placement into pens with a commercial coccidiosis vaccine (Coccivac-B). On days 20, 21 and 22 all birds, except Treatment 1, are dosed with a broth culture of *C. perfringens*. A field isolate of *C. perfringens* known to cause NE and originating from a commercial broiler operation is utilized as the challenge organism. Fresh inoculum is used each day. The titration levels are approximately $1.0\times 10^{8-9}$. Each pen receives the same amount of inoculum. The inoculum is administered by mixing into the feed found in the base of the tube feeder. On day 23, five birds from each pen are selected, euthanized, group weighed, and examined for the degree of presence of Necrotic Enteritis lesions. The scoring was based on a 0 to 3 score, with 0 being normal and 3 being the most severe (0=none, 1=mild, 2=moderate, 3=marked/severe; Hofacre et al., 2003 J. Appl. Poult. Res. 12:60-64). No concomitant drug therapy is used during the study.

Means are separated using pair wise t-tests. Significant differences are considered at P<0.05. Pens are used as the experimental unit.

Results

Body weight gain is significantly reduced by the *C. perfringens* challenge as shown from d23 until the end of the trial (FIG. 1). Supplementation with Enviva Pro significantly improves body weight gain to the level of the positive control on each of the sample days. However further supplementation with a high phytase dose (treatment 10) improved body weight to a level significantly greater than the positive control at days 12, 23 and 35 and a numerically greater level at d42.

Feed conversion ratio (FCR) is significantly increased by the *C. perfringens* challenge as shown form d 23 until the end of the trial (FIG. 2). Addition of Enviva Pro to the diet lead to a significant reduction in FCR from the negative control. However, supplementation with the high phytase dose reduces the FCR to a level the same as found in the positive control.

There is a reduction in mortality observed with the supplementation of Enviva Pro (FIG. 3), which is further numerically reduced with the supplementation of the high phytase dose. This can be accounted for by a reduction in the severity of the *C. perfringens* challenge, supported by the numerically reduced lesion scores found when the high phytase dose is supplemented (FIG. 4), which was not significantly different from the lesion scores of the positive control.

There is a clear benefit of utilising a high phytase dose (3000 FTU/kg) in combination with Enviva Pro, demonstrated with reduced FCR and increased body weight gain compared to using Enviva Pro with a standard (500 FTU) dose of phytase. These benefits are accounted for by reduced intestinal damage.

Example 2

Materials and Methods

A total of 1040 one-day-old Cobb×Cobb 500 male chicks are purchased from a commercial hatchery. At study initiation, ten males are randomly allocated to Petersime battery cages according to the respective treatments by blocks. Only healthy birds are selected for the experiment, and no birds are replaced throughout the course of the study. The study consists of the following treatments (Table 1):

TABLE 1

Experimental design of Example 2.

| Dietary Treatment | *Clostridium perfringens* Challenge | Dietary AvP level (%) | Phytase (Axtra Phy[2]) | Enviva Pro[1] 75,000 cfu/g feed |
|---|---|---|---|---|
| 1. Non challenged positive control | No | 0.4 | 0 | No |
| 2. Challenged positive control | Yes | 0.4 | 0 | No |
| 3. Non challenged negative control | No | 0.18 | 0 | No |
| 4. Challenged negative control (CNC) | Yes | 0.18 | 0 | No |
| 5. CNC + 500 FTU | Yes | 0.18 | 500 | No |
| 6. CNC + 1500 FTU | Yes | 0.18 | 1500 | No |
| 7. CNC + 3000 FTU | Yes | 0.18 | 3000 | No |
| 8. CNC + 10000 FTU | Yes | 0.18 | 10,000 | No |
| 9. CNC + Enviva Pro (EP) | Yes | 0.18 | 0 | Yes |
| 10. CNC + 500 FTU + EP | Yes | 0.18 | 500 | Yes |
| 11. CNC + 1500 FTU + EP | Yes | 0.18 | 1500 | Yes |
| 12. CNC + 3000 FTU + EP | Yes | 0.18 | 3000 | Yes |

TABLE 1-continued

Experimental design of Example 2.

| Dietary Treatment | Clostridium perfringens Challenge | Dietary AvP level (%) | Phytase (Axtra Phy[2]) | Enviva Pro[1] 75,000 cfu/g feed |
|---|---|---|---|---|
| 13. CNC + 10000 FTU +EP | Yes | 0.18 | 10,000 | Yes |

[1]Enviva Pro is combination of *Bacillus subtilis* strains Bs2084, LSSAO1 and 15AP4, provided by Danisco A/S, dosed at 75,000 CFU/g of feed.
[2]AxtraPhy™ is a 6-phytase from *Buttiauxella*, provided by Danisco A/S Bird weights are recorded at study initiation (d 0) and on days 13, 21 and study termination (d 28). The cage is the experimental unit. Diets are fed in mash form, and are formulated to meet or exceed NRC standards (Table 2). The mixer is flushed to prevent cross contamination between rations. Samples are collected from each treatment diet from the beginning, middle and end of each batch and are mixed together for analysis of enzyme activity and DFM presence in feed.

TABLE 2

Experimental diet composition of Example 2.

| | Starter (0 to 9 days) | Grower (PC) (10 to 28 days) | Grower (NC) (10 to 28 days) |
|---|---|---|---|
| Ingredient (%) | | | |
| Maize | 46.59 | 54.94 | 56.69 |
| Maize DDGS | 7.00 | 7.00 | 7.00 |
| Soybean Meal 48% CP | 32.67 | 25.64 | 25.33 |
| Rice Bran | 5.00 | 5.00 | 5.00 |
| Pig/Poultry Fat | 4.03 | 3.11 | 2.53 |
| Lysine | 0.37 | 0.41 | 0.42 |
| DL-methionine | 0.36 | 0.32 | 0.31 |
| L-threonine | 0.15 | 0.15 | 0.16 |
| Salt | 0.38 | 0.35 | 0.35 |
| Limestone | 0.88 | 0.96 | 1.38 |
| Dicalcium phosphate | 2.08 | 1.60 | 0.33 |
| Vitamin and trace mineral premix | 0.50 | 0.50 | 0.50 |
| Calculated Nutrient Composition (%) | | | |
| CP | 22.66 | 20.00 | 20.00 |
| Energy, kcal/kg | 3035 | 3059 | 3059 |
| Digestible lysine | 1.27 | 1.14 | 1.14 |
| Digestible methionine | 0.66 | 0.60 | 0.60 |
| Digestible threonine | 0.80 | 0.72 | 0.72 |

All birds are fed a "commercial style" ration until day 9; from day 10 the treatment rations are fed. At the feed change, feeders are removed from pens, weighed back, emptied, and refilled with the appropriate treatment diet. On the final day of the study, feed is weighed. Pens are checked daily for mortality. When a bird is culled or found dead, the date and removal weight (kg) are recorded. A gross necropsy is performed on all dead or culled birds to determine the probable cause of death. Signs of Necrotic Enteritis are recorded. Ad-libitum feed of the appropriate treatment is available for the birds throughout the duration of the study.

Disease induction is according to the research site standard operating procedure (SOP). Briefly; on day 13, all birds are orally inoculated with *Eimeria maxima*, with inocula containing approximately 5,000 oocysts per bird. On day 18, all birds apart from treatments 1 and 3, receive a broth culture of *Clostridium perfringens* containing approximately $10^8$ cfu/ml. All treated pens receive the same amount of inocula. Fresh *C. perfringens* inoculum is administered once daily for three days (days 18, 19 and 20) by mixing into the feed in the base of the feeders. On day 21, three birds from each pen are selected, euthanized, group weighed, and examined for the degree of presence of Necrotic Enteritis lesions. The scoring is based on a 0 to 3 score, with 0 being normal and 3 being the most severe (0=none, 1=mild, 2=moderate, 3=marked/severe; Hofacre et al., 2003 J. Appl. Poult. Res. 12:60-64). No concomitant drug therapy is used during the study.

For performance data, the effects of treatment are tested using ANOVA, and means are separated using pair wise t-tests using JMP software. Significant differences are considered at P<0.05. Cages are used as the experimental unit. For pH and organ weight data, each bird is an experimental unit.

In order to test interactions, a subset of treatments (treatments 4 to 13) are analysed with ANOVA using a factorial arrangement that included the main effects of phytase and Enviva Pro, as well as their interaction.

Results

The *C. perfringens* challenge significantly reduce bird performance in terms of both body weight gain (BWG) and feed conversion ratio (FCR), at both d 21 and d 28, compared to the unchallenged control (T1 vs. T2, T3 vs. T4) (Table 3). The reduction in dietary P has no effect on BWG at either d 21 or d 28 in the absence of the *C. perfringens* challenge. There is however, a noticeable numerical reduction in BWG between the high and low P diets in the presence of the *C. perfringens* challenge. These observations are consistent with the data for FCR.

When phytase is supplemented alone, there are variable effects on bird performance; however, in all cases, there is a numerical improvement in day 21 BWG to a level higher than that of the challenged low P diet (T4). Results obtained indicate that high phytase doses do not further improve bird performance in the conditions of a Necrotic Enteritis challenge; as the lowest BWG of the phytase only treatments is found at the 10,000 FTU dose of phytase (T8), which is not significantly different than the challenged low P diet (T4). Likewise, at day 28, when phytase is supplemented alone there is a numerical reduction in BWG at phytase levels greater than 1500 FTU.

When Enviva Pro is supplemented alone (T9) there is a significant improvement in BWG at day 21 from the challenged low P diet (T4) and a further improvement to a level not significantly different to the unchallenged low P diet by day 28. In terms of FCR, there is a significant reduction from the challenged control with Enviva Pro supplementation, but not enough to completely counteract the negative effects of the challenge.

Figure 5:
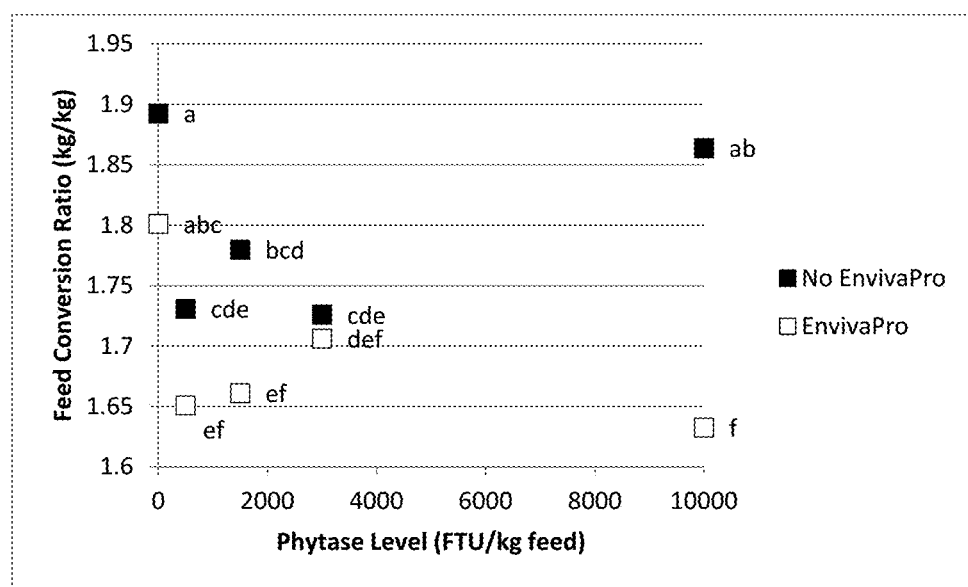
FIG. 5 shows the effect of different doses of phytase on FCR of broilers from 0 to 21 d in the presence and absence of Enviva Pro, under a Necrotic Enteritis challenge.

In combination, high doses of Phytase and Enviva Pro result in a more uniform response in terms of BWG, compared to when Phytase is supplemented alone, at both day 21 and day 28. In terms of FCR, there is a synergistic effect of the combination at day 21 (FIG. 5). When phytase is supplemented alone, there is an increase in performance (reduction in FCR) at the 500, 1500 (T7) and 3000 FTU/kg levels and a reduction in performance when phytase dose is exceeded in the conditions of a Necrotic Enteritis challenge. However, when the probiotic is added in combination, there consistently is a numerical reduction in the FCR compared to the phytase only treatments up to and including the level of 3000 FTU (T12). However at 10,000 FTU (T13), there is a large significant reduction which results in the lowest FCR of all of the treatment groups. When specifically investigating the effects of the combination (i.e. excluding positive controls T1, T2 and T3) there is a significant effect of the combination on day 21 FCR (P=0.0319) (Table 4).

The reduction in dietary AvP causes significant reductions in tibia ash (Table 3), which is an indicator of phosphorus bioavailability. The *C. perfringens* challenge results in small numerical reductions in tibia ash content, which is likely due to the intestinal damage caused by the infection reducing the ability of the gut to absorb nutrients efficiently. Supplementation with phytase alone results in restoration of the tibia ash % to a level not significantly different to the unchallenged high P diet (T1). When Enviva Pro is supplemented alone (T9), there is a numerical increase in tibia ash % to a level greater than the unchallenged low P diet (T3), which demonstrates the ability of the product to counter the effects of the *C. perfringens* challenge in terms of reductions in tibia ash, which could suggest restoration of gut function. When the combination was supplemented, there is a dose response to phytase reaching a level greater than the unchallenged high P diet (T1) at 3000 FTU, such an improvement is not observed when phytase was supplemented alone The *C. perfringens* challenge has a significant effect on mortality and lesion scores (Table 4). The lack of mortality and absence of lesion scores in the unchallenged groups indicates there is no contamination between challenged and unchallenged groups. There is no significant difference between the Phytase and EnvivaPro+Phytase at any level of phytase in terms of lesions scores (T4-8 vs. T9-13). However, there is a numerical increase in mortality above the level of the challenged low P diet in the Phytase only treatments for the 1500 (T6) and 3000 FTU (T7) treatments. The addition of EnvivaPro leads to a significant reduction in mortality from the challenged low P diet and also reduced the variation in mortality rates between the phytase doses in combination compared to the Phytase only treatments.

TABLE 3

The effect of Treatment on performance parameters; feed intake, body weight gain, feed conversion ratio and bone ash data at d21

| Dietary Treatment | Feed Intake | | Body Weight Gain | | Feed Conversion Ratio | | % Bone Ash |
|---|---|---|---|---|---|---|---|
| | d21 | d28 | d21 | d28 | d21 | d28 | |
| 1. Non challenged positive control | 6.587 e | 9.829 ab | 0.454 a | 0.943 ab | 1.453 g | 1.484 h | 16.03 Ab |
| 2. Challenged positive control | 7.390 a | 8.374 de | 0.410 bcd | 0.828 ef | 1.836 ab | 1.780 ab | 15.53 Bc |
| 3. Non challenged negative control | 6.903 bcde | 10.489 a | 0.463 a | 0.969 a | 1.501 g | 1.507 gh | 13.95 Ef |
| 4. Challenged negative control (CNC) | 7.319 ab | 8.887 cd | 0.387 d | 0.796 f | 1.893 a | 1.838 a | 13.71 F |
| 5. CNC + 500 FTU | 7.278 abc | 8.433 cde | 0.424 b | 0.884 bcde | 1.731 cde | 1.662 cde | 15.55 abc |
| 6. CNC + 1500 FTU | 7.003 abcde | 7.923 e | 0.397 bcd | 0.899 bcd | 1.780 bcd | 1.742 bc | 15.57 abc |
| 7. CNC + 3000 FTU | 7.175 abcd | 8.228 de | 0.414 bcd | 0.869 cde | 1.726 cde | 1.716 bc | 15.68 abc |
| 8. CNC + 10000 FTU | 7.317 ab | 8.118 de | 0.393 cd | 0.848 def | 1.864 ab | 1.721 bc | 16.18 ab |
| 9. CNC + Enviva Pro (EP) | 7.435 a | 9.345 bc | 0.422 b | 0.908 abcd | 1.801 bc | 1.688 cd | 14.19 ef |
| 10. CNC + 500 FTU + EP | 6.833 cde | 8.094 de | 0.418 bc | 0.938 ab | 1.651 ef | 1.600 def | 14.48 de |
| 11. CNC + 1500 FTU + EP | 6.874 bcde | 8.057 de | 0.421 bc | 0.931 abc | 1.661 ef | 1.493 gh | 15.03 cd |
| 12. CNC + 3000 FTU + EP | 7.003 abcde | 8.028 de | 0.420 bc | 0.936 ab | 1.706 def | 1.546 fgh | 16.27 a |
| 13. CNC + 10000 FTU + EP | 6.782 de | 8.587 cde | 0.421 bc | 0.905 abcd | 1.633 f | 1.566 efg | 16.00 ab |
| Standard Error | 0.182 | 0.348 | 0.0107 | 0.0237 | 0.0334 | 0.0343 | 0.269 |
| Effect tests | | | | | | | |
| Treatment | 0.0086 | <0.0001 | <0.0001 | <0.0001 | <0.0001 | <0.0001 | <0.0001 |

TABLE 4

Significant effect of the combination of Phytase + Enviva Pro on day 21 FCR.

| Dietary Treatment | FCR (0-21 d) |
|---|---|
| 4. Challenged positive control (CNC) | 1.893 a |
| 5. CNC + 500 FTU | 1.731 cde |
| 6. CNC + 1500 FTU | 1.780 bcd |
| 7. CNC + 3000 FTU | 1.726 cde |
| 8. CNC + 10000 FTU | 1.864 ab |
| 9. CNC + Enviva Pro (EP) | 1.801 abc |
| 10. CNC + 500 FTU + EP | 1.651 ef |
| 11. CNC + 1500 FTU + EP | 1.661 ef |
| 12. CNC + 3000 FTU + EP | 1.706 def |
| 13. CNC + 10000 FTU + EP | 1.633 f |
| Standard Error | 0.0328 |
| Effect tests | |
| Phytase | 0.0001 |
| Enviva Pro | <.0001 |
| Phytase*Enviva Pro | 0.0319 |

TABLE 5

The effect of Treatment on Mortality (%) and
Necrotic enteritis (NE) lesion scores.

| Dietary Treatment | NE lesion Score | % NE Mortality |
|---|---|---|
| 1. Non challenged positive control | 0.000 e | 0 d |
| 2. Challenged positive control | 0.830 abcd | 28.8 a |
| 3. Non challenged negative control | 0.000 e | 0 d |
| 4. Challenged negative control (CNC) | 0.580 cd | 27.5 ab |
| 5. CNC + 500 FTU | 0.830 abcd | 20 bc |
| 6. CNC + 1500 FTU | 1.340 a | 31.3 a |
| 7. CNC + 3000 FTU | 0.790 bcd | 31.3 a |
| 8. CNC + 10000 FTU | 1.250 ab | 27.5 ab |
| 9. CNC + Enviva Pro (EP) | 0.390 de | 16.3 c |
| 10. CNC + 500 FTU + EP | 0.980 abc | 18.8 c |
| 11. CNC + 1500 FTU + EP | 1.160 ab | 17.5 c |
| 12. CNC + 3000 FTU + EP | 0.890 abcd | 17.5 c |
| 13. CNC + 10000 FTU + EP | 1.080 abc | 17.5 c |
| Standard Error | 0.193 | 0.294 |
| Effect tests | | |
| Treatment | <0.0001 | <0.0001 |

Example 3

Methods

A total of 1080 one day old chicks are purchased from a commercial hatchery. At study initiation 15 chicks are randomly allocated to each pen by blocks. The study consists of the following treatments (table 1) and there are 8 replicate pens per treatment.

TABLE 1

Experimental design

| Dietary Treatment | Av. P (Starter/ Finisher) | DFM (CFU/g feed)[1] | Axtra Phy[2] (FTU/kg) |
|---|---|---|---|
| 1. Positive control | 0.45/0.42 | No | 0 |
| 2. Negative control (NC) | 0.20/0.20 | No | 0 |
| 3. NC + 500 FTU | 0.20/0.20 | No | 500 |
| 4. NC + 1500 FTU | 0.20/0.20 | No | 1500 |
| 5. NC + 3000 FTU | 0.20/0.20 | No | 3000 |
| 6. NC + Enviva Pro (EP) | 0.20/0.20 | Enviva Pro (7.5 × 10$^4$ cfu/g) | 0 |
| 7. NC + 500 FTU + EP | 0.20/0.20 | Enviva Pro (7.5 × 10$^4$ cfu/g) | 500 |
| 8. NC + 1500 FTU + EP | 0.20/0.20 | Enviva Pro (7.5 × 10$^4$ cfu/g) | 1500 |
| 9. NC + 3000 FTU + EP | 0.20/0.20 | Enviva Pro (7.5 × 10$^4$ cfu/g) | 3000 |

[1]Enviva Pro ® is combination of *Bacillus subtilis* strains Bs2084, LSSAO1 and 15AP4, provided by Danisco A/S.
[2]Axtra Phy is a 6-phytase from *Butiauxella* available from Danisco Animal Nutrition Bird weights are recorded at study initiation (day 0), day 6, day 21 and study termination (day 35). The pen is the unit of measure. Diets are formulated to meet NRC guidelines (Table 2). All treatment feeds are mixed using a Davis S-20 mixer. The mixer is flushed between diets to prevent cross contamination of diets. Samples are collected from each treatment diet form the beginning, middle and end of each batch, pooled, and analysed to confirm enzyme activity and DFM presence in feed. Diets are fed in mash form.

All pens have approximately 4 inches of built up litter with a coating of fresh pine shavings. All birds receive a commercial coccidiosis vaccine orally prior to placement into pens.

TABLE 2

Experimental diet composition

| | | Grower | | Finisher | |
|---|---|---|---|---|---|
| | Starter | PC | NC | PC | NC |
| Ingredient (%) | | | | | |
| Maize | 52.42 | 56.39 | 58.56 | 60.48 | 62.29 |
| US Maize DDGS | 7 | 7 | 7 | 7 | 7 |
| Soybean Meal 48% CP | 26.13 | 22.13 | 21.93 | 18.12 | 17.96 |
| Canola Meal | 3 | 3 | 3 | 3 | 3 |
| Feather Meal | 3 | 3 | 3 | 3 | 3 |
| Pig/Poultry Fat | 3.57 | 4.26 | 3.49 | 4.45 | 3.81 |
| L-Lysine HCl | 0.52 | 0.43 | 0.43 | 0.38 | 0.39 |
| DL-methionine | 0.33 | 0.26 | 0.26 | 0.21 | 0.21 |
| L-threonine | 0.13 | 0.08 | 0.08 | 0.06 | 0.05 |
| Salt | 0.35 | 0.35 | 0.35 | 0.35 | 0.35 |
| Limestone | 0.97 | 0.76 | 1.02 | 0.75 | 1.03 |
| Dicalcium Phosphate | 2.09 | 1.84 | 0.38 | 1.70 | 0.42 |
| Poultry Vits/TE's | 0.5 | 0.5 | 0.5 | 0.5 | 0.5 |
| Calculated Nutrient Composition | | | | | |
| Crude Protein (%) | 23.0 | 21.3 | 21.4 | 19.6 | 19.7 |
| Energy MJ/Kg | 12.65 | 13 | 13 | 13.2 | 13.2 |
| Dig. Lysine (%) | 1.27 | 1.1 | 1.1 | 0.97 | 0.97 |
| Dig. Methionine + Cystine (%) | 0.94 | 0.84 | 0.84 | 0.76 | 0.76 |
| Dig. Threonine (%) | 0.83 | 0.73 | 0.73 | 0.65 | 0.65 |
| Available P (%) | 0.5 | 0.45 | 0.2 | 0.42 | 0.2 |

All birds are fed a commercial style starter ration from day 0-6. From day 7 grower diets appropriate to the treatment are fed until day 21. Finisher diets appropriate to treatment are fed from day 21 to study termination (day 35). At the feed change, feeders are removed from pens, weighed back, emptied, and refilled with the appropriate treatment diet. On the final day of the study, feed is weighed. Pens are checked daily for mortality. When a bird is culled or found dead, the date and removal weight (kg) are recorded.

For performance data, means are separated using pair wise t-tests. Significant differences are considered at $P<0.05$. Pens are used as the experimental unit.

Results

Figure 6:
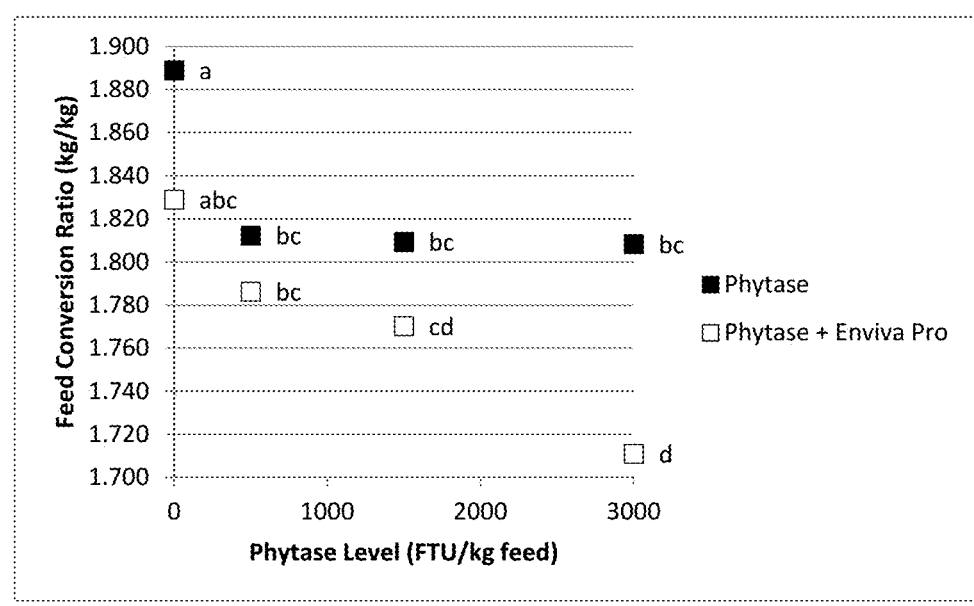
FIG. 6 shows the effect of different doses of phytase on FCR of broilers from day 6-35.

Increasing the dose of phytase alone causes no significant improvement in feed conversion ratio (FCR) at 35 days of age (FIG. 6). The addition of Enviva Pro at all levels of phytase reduces FCR. As phytase dose increases so does the benefit from adding Enviva Pro. The highest level of phytase inclusion creates the largest difference in FCR between the diets with and without Enviva Pro.

TABLE 3

Performance results

| Dietary Treatment | Body weight gain (g/bird) Day 35 | Feed intake (g/bird) Day 6-35 | FCR (g BWG/g FI) Day 6-35 |
|---|---|---|---|
| 1. Positive control | 1961.1$^a$ | 3225.5$^a$ | 1.856$^{ab}$ |
| 2. Negative control (NC) | 1785.9$^b$ | 2953.3$^{bc}$ | 1.889$^a$ |
| 3. NC + 500 FTU | 1976.8$^a$ | 3158.4$^a$ | 1.812$^{bc}$ |
| 4. NC + 1500 FTU | 2009.4$^a$ | 3196.9$^a$ | 1.809$^{bc}$ |
| 5. NC + 3000 FTU | 2007.3$^a$ | 3175.6$^a$ | 1.808$^{bc}$ |
| 6. NC + Enviva Pro (EP) | 1757.1$^b$ | 2787.9$^c$ | 1.829$^{abc}$ |
| 7. NC + 500 FTU + EP | 1947.8$^a$ | 3065.1$^{ab}$ | 1.786$^{bc}$ |
| 8. NC + 1500 FTU + EP | 2020.5$^a$ | 3164.9$^a$ | 1.770$^{cd}$ |
| 9. NC + 3000 FTU + EP | 2026.1$^a$ | 3049.0$^{ab}$ | 1.711$^d$ |
| SEM | 34.33 | 64.19 | 0.0252 |
| Source of Variation Treatment | <0.0001 | 0.0001 | 0.0006 |

At higher doses of phytase, there is a numerical increase in body weight gain (BWG) when Enviva Pro is supplemented compared to when phytase is supplemented alone (Table 3). This effect is not seen at the lowest dose (500 FTU) of phytase.

Example 4

Materials and Methods

One day old Cobb male chicks are purchased from a commercial hatchery. At study initiation, ten males are randomly allocated to each battery cage by blocks. There are eight replicate cages per treatment. The study consists of the following treatments (Table 1).

TABLE 1

Experimental Design of Example 4

| Treatment | Clostridium perfringens Challenge | Available P in diet (%) | Phytase | Amount (FTU/kg feed) | DFM (CFU/g feed)[2] |
|---|---|---|---|---|---|
| 1 | No | 0.4 | None | 0 | None |
| 2 | Yes | 0.4 | None | 0 | None |
| 3 | No | 0.18 | None | 0 | None |
| 4 | Yes | 0.18 | None | 0 | None |
| 5 | Yes | 0.18 | HiPhos[1] | 500 | None |
| 6 | Yes | 0.18 | HiPhos[1] | 1500 | None |
| 7 | Yes | 0.18 | HiPhos[1] | 3000 | None |
| 8 | Yes | 0.18 | None | 0 | Enviva Pro ($7.5 \times 10^4$ FTU/g) |
| 9 | Yes | 0.18 | HiPhos[1] | 500 | Enviva Pro ($7.5 \times 10^4$ FTU/g) |
| 10 | Yes | 0.18 | HiPhos[1] | 1500 | Enviva Pro ($7.5 \times 10^4$ FTU/g) |
| 11 | Yes | 0.18 | HiPhos[1] | 3000 | Enviva Pro ($7.5 \times 10^4$ FTU/g) |

[1]HiPhos is Ronozyme HiPhos and contains a phytase from *Citrobacter braakii* and is available from DSM/Novozymes
[2]Enviva Pro ® is combination of *Bacillus subtilis* strains Bs2084, LSSAO1 and 15AP4, provided by Danisco A/S.

Bird weights are recorded at study initiation (0 d), day 21 and termination (28 d). The cage is the unit of measure. Diets meet or exceed NRC standards (Table 2). All treatment feeds are mixed using a Davis S-20 mixer. The mixer is flushed between diets to prevent cross contamination of diets. Samples are collected from each treatment diet from the beginning, middle, and end of each batch and blended together to confirm enzyme activities and Enviva Pro presence in feed.

TABLE 2

Experimental diet composition of Example 4

| | Starter (0 to 9 days) | Grower (PC) (10 to 28 days) | Grower (NC) (10 to 28 days) |
|---|---|---|---|
| Ingredient (%) | | | |
| Maize | 46.59 | 54.94 | 56.69 |
| Maize DDGS | 7.00 | 7.00 | 7.00 |
| Soybean Meal 48% CP | 32.67 | 25.64 | 25.33 |
| Rice Bran | 5.00 | 5.00 | 5.00 |
| Pig/Poultry Fat | 4.03 | 3.11 | 2.53 |
| Lysine | 0.37 | 0.41 | 0.42 |
| DL-methionine | 0.36 | 0.32 | 0.31 |
| L-threonine | 0.15 | 0.15 | 0.16 |
| Salt | 0.38 | 0.35 | 0.35 |
| Limestone | 0.88 | 0.96 | 1.38 |
| Dicalcium phosphate | 2.08 | 1.60 | 0.33 |
| Vitamin and trace mineral premix | 0.50 | 0.50 | 0.50 |
| Calculated Nutrient Composition (%) | | | |
| CP | 22.66 | 20.00 | 20.00 |
| Energy, kcal ME/kg | 3035 | 3059 | 3059 |
| Digestible lysine (%) | 1.27 | 1.14 | 1.14 |
| Digestible methionine (%) | 0.66 | 0.60 | 0.60 |
| Digestible threonine (%) | 0.80 | 0.72 | 0.72 |

All birds are fed a commercial pre-starter ration until day 9; from day 10 the treatment rations are fed. At the feed change, feeders are removed from cages, weighed back, emptied, and refilled with the appropriate treatment diet. On the final day of the study, feed is weighed. Cages are checked daily for mortality. When a bird is culled or found dead, the date and removal weight (kg) are recorded. A gross necropsy is performed on all dead or culled birds to determine the probable cause of death. Signs of Necrotic Enteritis are recorded. Ad-libitum feed of the appropriate treatment is available for the birds throughout the duration of the study. Disease induction is according to the research site standard operating procedure (SOP). Briefly; on day 13, all birds we orally inoculate with *Eimeria maxima*, with inocula containing approximately 5,000 oocysts per bird. On day 18, all birds apart from treatments 1 and 3, receive a broth culture of *Clostridium perfringens* containing approximately 108 cfu/ml. All treated pens receive the same amount of inocula. Fresh *C. perfringens* inoculum is administered once daily for three days (days 18, 19 and 20) by mixing into the feed in the base of the feeders. On day 21, three birds from each pen are selected, euthanized, group weighed, and examined for the degree of presence of Necrotic Enteritis lesions. The scoring is based on a 0 to 3 score, with 0 being normal and 3 being the most severe (0=none, 1=mild, 2=moderate, 3=marked/severe; Hofacre et al., 2003 J. Appl. Poult. Res. 12:60-64). No concomitant drug therapy is used during the study.

The pH of ileal digesta of 2 birds per cage is measured on day 21. The pH of the digesta is determined by inserting a Sensorex spear tip piercing pH probe into the respective sections. In both birds, the gizzards are also removed and weighed. On day 21, the right tibias of the two birds are removed, dried overnight at 100° C. and weighed; samples are then fat-extracted and burned in a muffle furnace at 600° C. for 16 hours to determine the fat free bone ash. The percentage bone ash is then calculated as the ratio of remaining ash weight to the dry-fat free bone weight multiplied by 100.

Statistical Analysis

For performance data, means are separated using pair wise t-tests. Significant differences are considered at $P<0.05$. Cages are used as the experimental unit.

Figure 7:
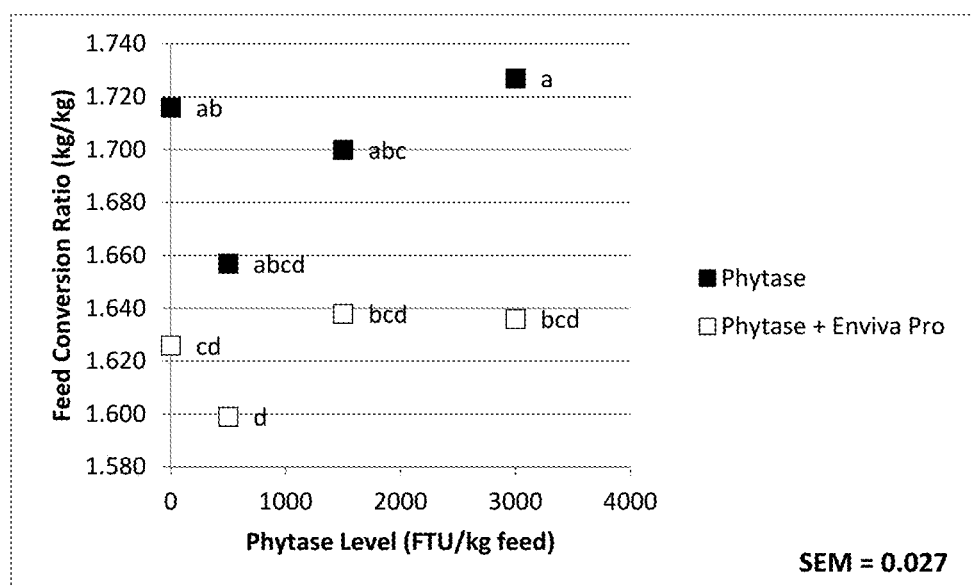
FIG. 7 shows the effect of different doses of HiPhos™ phytase on FCR of broilers from day 0 to 21 with and without Enviva Pro, under a Necrotic Enteritis challenge.

Results:

Increasing the dose of Hi Phos causes an increase in feed conversion ratio at 21 days of age (FIG. 7; more feed per unit of body weight gain) in a Necrotic Enteritis challenge situation. The addition of Enviva Pro at all levels of inclusion of phytase cause a decrease, improving FCR. At the highest level of phytase inclusion (3000 FTU/kg) the increase in FCR seen over the 1500 FTU/kg dose is increasingly attenuated by the addition of Enviva Pro.

TABLE 3

Performance results from Example 4

| Dietary Treatment | Feed Intake 0-21 d (g/bird) | FCR 0-21 d (g/g) | Body Weight Gain 0-21 d (g/bird) |
|---|---|---|---|
| PC | 524.052bc | 1.390d | 378ab |
| Unchallenged NC | 597.000ab | 1.450d | 412a |
| Challenged (Cc) PC | 480.980c | 1.619c | 298d |
| Challenged (Cc) NC | 558.952ab | 1.716a | 326cd |
| Cc 500 HiPhos | 600.161a | 1.657abc | 366abc |
| Cc 1500 HiPhos | 611.731a | 1.700ab | 360bc |
| Cc 3000 HiPhos | 602.466a | 1.727a | 350bc |
| Cc + Enviva Pro (EP) | 585.231ab | 1.626bc | 361abc |
| Cc 500 HiPhos + EP | 554.078abc | 1.599c | 347bcd |
| Cc 1500 HiPhos + EP | 595.992ab | 1.638bc | 365abc |
| Cc 3000 HiPhos + EP | 611.336a | 1.636bc | 374abc |
| SEM | 26.456 | 0.027 | 18 |
| Source of Variation Treatment | <0.01 | <0.01 | <0.01 |

The body weight gain effect of Enviva Pro on top of phytase is more evident at high phytase doses (3000 FTU/kg), where the body weight gain was not significantly different compared to that in the unchallenged control treatment.

Figure 8:
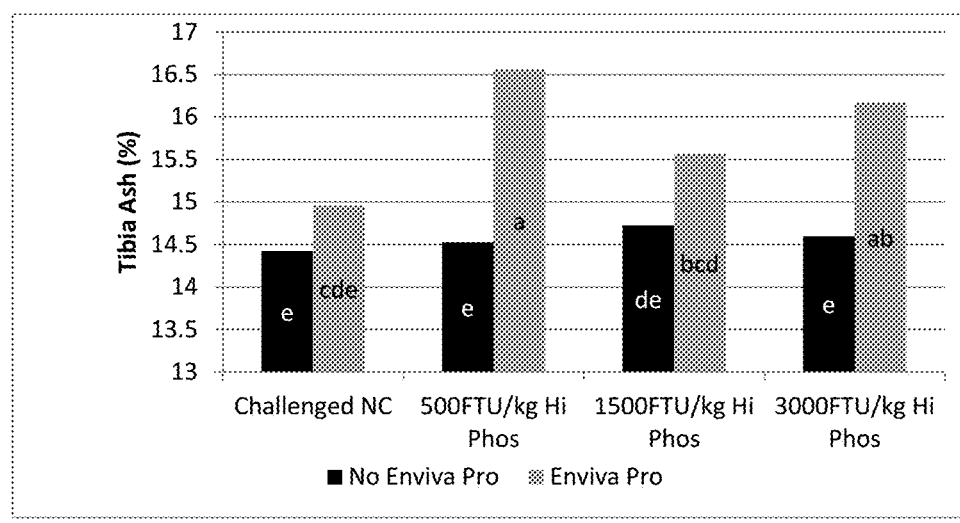
FIG. 8 shows the effect of different levels of HiPhos™ phytase with and without Enviva Pro on tibia ash of broilers at 21 days, under a Necrotic Enteritis challenge.

The effect of phytase on tibia ash percentage is not significantly different to the negative challenged control, suggesting that phytase does not have a significant effect on tibia ash under challenge situations, even at high doses (FIG. 8). The addition of Enviva Pro however acts to significantly improve tibia ash percentage to bring it close to that seen in the positive unchallenged control at the highest dose of phytase (3000 FTU/kg) as seen in Table 4.

TABLE 4

Other physiological measurements from Example 5

| Dietary Treatment | Tibia Ash (%) | Ileal pH at 21 d | Gizzard weight 21 d (g/bird) | Mortality (%) | Lesion Score (1-3 score) |
|---|---|---|---|---|---|
| PC | 16.520a | 6.116bcd | 24.356a | 0.000e | 0.000c |
| Unchallenged NC | 14.899cde | 6.326abc | 24.650a | 0.000e | 0.000c |
| Challenged (Cc) PC | 15.742abc | 6.298abc | 24.058ab | 15.000a | 0.417ab |
| Challenged (Cc) NC | 14.423e | 6.074cd | 20.275b | 11.250ab | 0.333abc |
| Cc 500 HiPhos | 14.526e | 6.420abc | 22.392ab | 5.000cde | 0.250abc |
| Cc 1500 HiPhos | 14.724de | 6.313abc | 23.123ab | 7.500bcd | 0.542a |
| Cc 3000 HiPhos | 14.597e | 6.540a | 20.261b | 8.750bc | 0.542a |
| Cc + Enviva Pro (EP) | 14.957cde | 5.889d | 23.506ab | 3.750cde | 0.375ab |
| Cc 500 HiPhos + EP | 16.560a | 6.398abc | 21.211ab | 2.500de | 0.500a |
| Cc 1500 HiPhos + EP | 15.567bcd | 6.486ab | 21.480ab | 6.250bcd | 0.125bc |
| Cc 3000 HiPhos + EP | 16.172ab | 6.389abc | 20.770ab | 7.500bcd | 0.375ab |
| SEM | 0.329 | 0.132 | 1.431 | 1.890 | 0.119 |
| Source of Variation Treatment | <0.001 | <0.05 | 0.226596 | <0.001 | <0.01 |

High levels of phytase (3000 FTU/kg) increase ileal pH at 21 d over the relevant control, and the addition of Enviva Pro act to reduce it, with the lowest pH seen with the Enviva Pro alone treatment. The lowest gizzard weights are seen in the challenged negative control and the highest dose of Hi Phos (3000 FTU/kg). The addition of Enviva Pro numerically increase gizzard weight at the 3000 FTU/kg dose but not significantly.

The challenge increases mortality significantly, with the addition of phytase acting to reduce it. The combination with Enviva Pro acted to reduce it further.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method for improving the performance of a subject or for improving digestibility of a raw material in a feed, or for improving nitrogen retention, or for improving dietary phosphorus absorption and retention, or for improving the efficacy of the phytase, or for improving the subject's resistance to necrotic enteritis or for improving feed conversion ratio (FCR) or for improving weight gain in a subject or for improving feed efficiency in a subject or for modulating the immune response of the subject or for reducing populations of pathogenic bacteria in the gastrointestinal tract of a subject, or for reducing nutrient excretion in manure, which method comprising administering to a subject at least one direct fed microbial comprising *Bacillus amyloliquefaciens* in combination with a phytase, wherein the phytase is administered to the subject at a dosage of more than about 1500 FTU/kg feed.

2. A method according to claim 1 wherein the direct fed microbial is an antipathogen direct fed microbial.

3. A method according to claim 1 wherein the direct fed microbial is a viable bacterium.

4. A method according to claim 1 wherein the phytase is administered to the subject at a dosage of more than about 2000 FTU/kg feed.

5. A method according to claim 1 wherein the phytase is administered to the subject at a dosage of more than about 3000 FTU/kg feed.

6. A method according to claim 1 wherein the composition comprises as least three direct fed microbials.

7. A method according to claim 1 wherein the direct fed microbial is a strain which inhibits intestinal establishment of pathogenic microorganisms.

8. A method according to claim 7 wherein the pathogenic microorganisms are *Clostridium perfringens* and/or *E. coli*.

9. A method according to claim 1 wherein the direct fed microbial further comprises a bacterium from one or more of the following genera: *Bacillus, Enterococcus, Pediococcus, Saccharomyces, Bifidobacterium, Propionibacterium, Lactobacillus, Lactococcus, Aspergillus* and combinations thereof.

10. A method according to claim 1 wherein the direct fed microbial further comprises a bacterium from one or more of the following species: *Bacillus subtilis, Bacillus licheniformis, Bacillus cereus, Enterococcus faecium, Pediococcus acidilactici, Saccharomyces cerevisiae, Bifidobacterium animalis* spp *animalis, Lactobacillus reuteri, Lactobacillus rhamnosus, Lactobacillus acidophilus, Lactobacillus brevis, Lactobacillus salivarius* ssp *salivarius, Lactobacillus farciminis, Lactococcus lactis, Lactobacillus casei, Lactobacillus salivarius, Clostridium butyricum, Aspergillus oryzae, Propionibacterium acidipropionici, Propionibacterium jensenii*, and combinations thereof.

11. A method according to claim 1 wherein the direct fed microbial further comprises one or more of the following strains: *Bacillus subtilis* BS18 (NRRL B-50633), *Bacillus subtilis* BS278 (NRRL 50634), *Bacillus subtilis* 4-7 d (NRRL B-50505), *Bacillus subtilis* 3-5 h (NRRL B-50507), *Bacillus subtilis* AGTP BS3BP5 (NRRL B-50510), *Bacillus subtilis* BS918 (NRRL B-50508), *Bacillus subtilis* AGTP BS1013 (NRRL-50509), *B. subtilis* AGTP 944 (NRRL B-50548), *Bacillus subtilis* AGTP BS442 (NRRL B-50542), *B. subtilis* AGTP BS1069 (NRRL B-50544), *B. subtilis* AGTP BS521 (NRRL B-50545), *B. subtilis* BS2084 (NRRL B-50013), *B. subtilis* LSSA01 (NRRL B-50104), *B. subtilis* B27 (NRRL B-50105), *B. subtilis* 3A-P4 (PTA-6506), *Bacillus subtilis* 15A-P4 (PTA-6507), *B. subtilis* 22C-P1 (PTA-6508), *B. subtilis* BL21 (NRRL B-50134), *Bacillus licheniformis* BL21 (NRRL B-50134), *Bacillus licheniformis* 3-12a (NRRL B-50504), *Bacillus licheniformis* 4-2a (NRRL B-50506), *Bacillus licheniformis* 842 (NRRL B-50516), *Propionibacterium acidipropionici* P261 (NRRL B-50131), *Propionibacterium acidipropionici* P179 (NRRL B-50133), *Propionibacterium acidipropionici* P169 (PTA 5271), *Propionibacterium acidipropionici* P170 (PTA 5272), *Propionibacterium jensenii* P63 (NRRL B-30979), *Propionibacterium jensenii* P195 (NRRL B-50132), *Lactococcus lactis* ID7 (PTA 6103), *Lactococcus lactis* JD19 (PTA 6104), *Lactobacillus acidophilus* A2020 (NRRL B-30977), *Lactobacillus acidophilus* A4000 h (NRRL B-30978), *Lactobacillus acidophilus* PIBc6 (NRRL B-50103), *Lactobacillus*

*brevis* LBR 1000 (NRRL B-30982), *Lactobacillus casei* LC222 (NRRL B-30983), *Lactobacillus johnsonii* PLCB6 (NRRL B-50518), *Lactobacillus salivarius* o246i33w (NRRL B-50102), *Lactobacillus brevis* AJ25 (PTA-6099), *Lactobacillus brevis* HE17 (PTA-6100), *Lactobacillus brevis* 1E-1 (PTA-6509), *Lactobacillus lactis* C115 (PTA-6101), *Lactobacillus lactis* DJ6 (PTA-6102), *Lactobacillus rhamnosus* (CNCM 1-3698), *Lactobacillus farciminis* (CNCM 1-3699), *Enterococcus faecium* EF141 (EN-1) (NRRL B-30981), *Enterococcus faecium* 2-1 d (NRRL B-50519), *Pediococcus acidilactici* PIJe3 (NRRL B-50101), *Pediococcus acidilactici* o246e42 (NRRL B-50171) and combinations thereof.

12. A method use according to claim 1 wherein the phytase is a 6-phytase or a 3-phytase.

13. A method according to claim 12 wherein the phytase is a 6-phytase.

14. A method according to claim 1 wherein the phytase is an *E. coli* phytase or a *Buttiauxella* phytase or a *Citrobacter* phytase or a Hafnia phytase or an *Aspergillus* phytase or a *Penicillium* phytase or a *Trichoderma* phytase or a *Pichia* phytase or a *Peniophora* phytase.

15. A method according to claim 1 wherein the DFM is present at a dosage of $3.75 \times 10^7$ CFU/g feed additive composition and $1 \times 10^{11}$ CFU/g feed additive composition.

16. A method according to claim 1 wherein a clinical or subclinical intestinal disease challenge is present in the subject.

17. A method according to claim 16 wherein the clinical or subclinical intestinal disease challenge may be caused by a pathogenic bacteria.

18. A method according to claim 17 wherein the pathogenic bacteria are *Clostridium perfringens* or *E. coli*.

* * * * *